US012642666B2

(12) United States Patent
Ryd et al.

(10) Patent No.: US 12,642,666 B2
(45) Date of Patent: Jun. 2, 2026

(54) METATARSAL IMPLANT

(71) Applicant: Episurf IP-Management AB, Stockholm (SE)

(72) Inventors: Leif Ryd, Malmö (SE); C. Niek van Dijk, Abcoude (NL)

(73) Assignee: Episurf IP-Management AB, Stockholm (SE)

( * ) Notice: Subject to any disclaimer, the term of this patent is extended or adjusted under 35 U.S.C. 154(b) by 0 days.

(21) Appl. No.: 19/264,343

(22) Filed: Jul. 9, 2025

(65) Prior Publication Data

US 2026/0060810 A1 Mar. 5, 2026

(30) Foreign Application Priority Data

Aug. 29, 2024 (WO) ................ PCT/EP2024/074209

(51) Int. Cl.
  *A61F 2/42* (2006.01)
  *A61F 2/30* (2006.01)

(52) U.S. Cl.
  CPC ........ *A61F 2/4225* (2013.01); *A61F 2/30771* (2013.01); *A61F 2/30942* (2013.01);
  (Continued)

(58) Field of Classification Search
  CPC ............................ A61F 2/4225; A61F 2/4241
  See application file for complete search history.

(56) References Cited

U.S. PATENT DOCUMENTS 5,774,203 A     6/1998 Diehl
7,208,222 B2 *  4/2007 Rolfe ..................... A61F 2/442
                                              428/137
(Continued)

FOREIGN PATENT DOCUMENTS

AU          776010 A1     7/2000
DE     101 30 796 A1     1/2003
(Continued)

OTHER PUBLICATIONS

Written Opinion and International Search Report issued Mar. 3, 2025 in Intl. Appl. No. PCT/EP2024/074209.

*Primary Examiner* — Marcia L Watkins
(74) *Attorney, Agent, or Firm* — MEDLER FERRO WOODHOUSE & MILLS PLLC

(57) ABSTRACT

A metatarsal implant for repairing damage in a metatarsophalangeal joint of a patient and in particular for repairing damage caused by osteofytes or as a result of osteofytes is provided. The metatarsal implant is adapted to be attached to an implant receiving surface at least partly covering a lateral surface of the metatarsal head. A bone contacting surface of the metatarsal implant is designed to correspond to the implant receiving surface, the bone contacting surface thus comprising at least two sub-surfaces in different planes, and at least one junction point where sub-surfaces meet, and a contour curvature of the articulating surface is designed by simulating a healthy articulating surface of the damaged metatarsal head, generated based on a determined surface curvature of the cartilage and/or the bone in a predetermined area at the site of diseased cartilage and/or bone, to mimic the original, undamaged, articulating surface of the metatarsal head.

21 Claims, 14 Drawing Sheets

(52) U.S. Cl.
CPC .............. *A61F 2002/30331* (2013.01); *A61F*
*2002/3093* (2013.01); *A61F 2002/30952*
(2013.01); *A61F 2002/3096* (2013.01); *A61F*
*2002/4233* (2013.01)

(56) References Cited

U.S. PATENT DOCUMENTS

| | | | | |
|---|---|---|---|---|
| 8,292,966 B2* | 10/2012 | Morton | ................. | A61B 17/15 |
| | | | | 623/21.19 |
| 9,888,931 B2 | 2/2018 | Bake | | |
| 11,607,319 B2* | 3/2023 | Ek | ......................... | A61F 2/4081 |
| 2010/0262254 A1 | 10/2010 | Lawrence et al. | | |
| 2011/0093084 A1 | 4/2011 | Morton | | |
| 2012/0215320 A1 | 8/2012 | Harber et al. | | |
| 2019/0231538 A1* | 8/2019 | Bake | ................. | A61B 17/1764 |
| 2019/0328548 A1 | 10/2019 | Bake et al. | | |
| 2020/0197183 A1* | 6/2020 | Nutter | ................. | A61F 2/3804 |
| 2021/0059829 A1 | 3/2021 | Montross et al. | | |
| 2024/0325154 A1* | 10/2024 | Ryd | ................. | A61B 17/1775 |
| 2024/0390155 A1* | 11/2024 | Ryd | ...................... | A61B 17/15 |

FOREIGN PATENT DOCUMENTS

| | | | |
|---|---|---|---|
| EP | 3013256 | B1 | 11/2018 |
| FR | 2733412 | A1 | 10/1996 |
| WO | 2006052874 | A2 | 5/2006 |
| WO | 2009073924 | A1 | 6/2009 |
| WO | 2023046983 | A1 | 3/2023 |

* cited by examiner

300

310

340

320

330

335

332

333

300

331

1

METATARSAL IMPLANT

CROSS-REFERENCE TO RELATED APPLICATIONS

This application claims priority to PCT International Application No. PCT/EP2024/074209 filed Aug. 29, 2024, which is incorporated herein in its entirety.

TECHNICAL FIELD

The present disclosure relates generally to implants suitable for repairing damage in the toe of a patient, such as e.g. a big toe, especially damage in the metatarsophalangeal joint of a patient and in particular for repairing a joint affected by osteoarthritic damage and osteophytes.

BACKGROUND

Implants for metatarsophalangeal joints often limit the dorsiflexion of the toe, and therefore often do not give the patient back a full range of motion. One reason for this may be that they do not take full account of the sesamoid bones, which move around the metatarsal head as the toe is bent. Another reason is osteophytes (or spurs), which also limit the motion of the toe. The first metatarsophalangeal joint is a hallux (big toe) joint that consists of the articulation between the first metatarsal head and the first proximal phalanges, as well as the articulation between the plantar aspect of the first metatarsal head and the sesamoid bones. The range of motion of the unaffected first metatarsophalangeal joint is largest in the sagittal plane and ranges between approximately 15° of plantar flexion to 75° dorsiflexion from standing position. The normal range of motion is approximately 65-100°.

The first metatarsal joint consists of the first metatarsal bone which articulates with the first proximal phalanx. The angle between these two bones is called the Metatarso-Phalangeal Angle (MPA). In the normal adult population, the mean MPA is 5.5+5.1° (Ali-Asgar Najefi et al Foot and Ankle int.2021) Wearing tight footwear with a pointed toe-box increases the valgus position of the big toe which results in an increased MPA (Inman1974, Muneanu et al 2017).

Around 40% of body weight is imposed on the toes in the final stage of foot contact. Most of this force is imposed on the 1$^{st}$ MTP (metatarsophalangeal) joint of the big toe (600 N) Walking produces a large axial force on the 1$^{st}$ MTP joint (J. Anat 1979 129, 3 579-590 Stokes IAF forces acting on the metatarsals during normal walking).

Because of the valgus position, the forces act asymmetrically on the head, the lateral part being exposed to a higher load. This can result in reactive bone spur (osteophyte) formation and hallux rigidus. These reactive spurs occur in the area of most load which is the lateral side of the joint. These osteophytes limit the motion of the joint (hallux limitus and hallux rigidus).

Hallux limitus (limited range of motion of the 1$^{st}$ MTP joint) is considered an earlier stage of progressive osteoarthritic disorder of the 1$^{st}$ MTP joint, due to acute or chronic injury to the 1$^{st}$ MTP joint, or of the rheumatoid arthritis, with genetic, autoimmune and inflammatory components. Hallux limitus may advance to the end-stage hallux rigidus, where the joint loses its full range of motion. Hallux rigidus is associated with painful stiffness of the big toe and is manifested by a decreased total arc of motion with near normal plantar flexion and a decreased dorsiflexion, secondary to a mechanical block by osteophytes (immature bone formation, also named bony spurs) and scarring of the plantar structures. The transversal motion of approximately 2 mm in the normal toe may be 50% reduced in hallux rigidus, and this is thought to be due to the contracture of the collateral ligaments and the joint capsule.

The 1$^{st}$ MTP joint supports considerable mechanical loads during activity, even though it is not a direct weight-bearing articulation. High compressive loads are produced by associated muscle action. Stability of the 1$^{st}$ MTP joint is important for the stability of the medial column of the foot. Furthermore, the 1$^{st}$ MTP joint is subject to flexion, extension, abduction/adduction and pronation/supination forces. Shear stress is dissipated by dorsal gliding of the phalanx on the native metatarsal head, which spares the joint during gait, making it an ideal joint for hemiarthroplasty.

A number of different resurfacing implants for the MTP joint are known. Examples are shown e.g. in AU776010, WO2006052874, WO2009073924, US20100262254, US20120215320, and US20210059829. U.S. Pat. No. 9,888,931 describes a guide tool that is adapted for repair of damage in a finger or a toe. WO2009073924 describes an embodiment of an endoprosthesis for an MTP joint, and U.S. Pat. No. 5774203 describes a prosthetic joint for replacing the natural metatarsal-phalangeal-sesamoid joint of the toe. EP3013256 and US2019328548 describe guide tools that may be used for repairing damage in e.g. toes using a small implant placed in a hole that is drilled in the surface of the metatarsal bone.

Implants for MTP joints often limit the dorsiflexion of the toe, and therefore often do not give the patient back a full range of motion. One reason for this is that they do not take full account of the sesamoid bones, which move around the metatarsal head as the toe is bent. Another reason may be that raw bone surfaces after osteophyte/bone spurs removal cause friction in the joint, which may be particularly occurring on a lateral side of the MTP joint.

In case of operative treatment for hallux rigidus these osteofytes must be removed in order to liquidate the restriction of motion.

Removal of these osteophytes results in a raw bone surface. After surgery the toe is immobilized. The capsule, synovium and subcutaneous tissue sticks and gets fixed to this raw bone surface, thereby limiting the future motion of the big toe. This process is called arthrofibrosis.

Therefore, there is a need for improved implants suitable for repairing damage in the toes of a patient and in particular, a toe implant suitable for repairing damage caused by osteophytes or as a result of osteophytes.

SUMMARY

The above described problems are addressed by the claimed metatarsal implant comprising a lateral flange for repairing damage in an MTP joint of a patient and in particular for repairing a joint affected by osteoarthritic damage including osteophytes. The metatarsal implant is adapted to be attached to an implant receiving surface which has been created on a metatarsal head of the patient by mechanical preparation of the metatarsal head to create at least one implant receiving surface on a lateral surface, for example by removing parts of the metatarsal head by means of drilling, sawing or milling. Preferably, implant receiving surfaces are created on the metatarsal head, including a lateral surface, in at least two different planes, which in some embodiments may have a predetermined angle therebetween.

A lateral flange which covers the raw bone surface will prevent adherence of the joint capsule to the lateral side of the metatarsal bone. The lateral flange of the implant preferably has highly polished surfaces providing smooth surfaces or interfaces toward the bone and the tissue thereby accommodating full range of motion of the joint and preventing arthrofibrosis.

A bone contacting surface of the metatarsal implant is designed to correspond to the implant receiving surfaces, the bone contacting surface comprising at least two different sub-surfaces, including a lateral surface, in different planes with a corresponding predetermined implant angle therebetween, and a contour curvature of an articulating surface of the metatarsal implant is designed to repair a damaged metatarsal head, for example by using a standardized implant or by simulating a healthy articulating surface of the damaged metatarsal head, generated based on a determined surface curvature of the cartilage and/or the bone in a predetermined area at a site of diseased cartilage and/or bone, to mimic the original, undamaged, articulating surface of the metatarsal head. This enables the repairing of damage in a MTP joint of a patient with a metatarsal implant that takes full account of the sesamoid bones and may also extend far enough to always interact with the sesamoid bones.

Moreover, the above-described problem is addressed by the claimed metatarsal implant comprising a lateral flange for repairing damage in an MTP joint of a patient. The metatarsal implant is adapted to be attached to an implant receiving surface which has been created on a metatarsal head of the patient by mechanical preparation of the metatarsal head to create implant receiving surfaces in at least two different planes, in some embodiments with a predetermined angle therebetween. A bone contacting surface of the metatarsal implant is designed to correspond to the implant receiving surfaces, the bone contacting surface thus comprising at least two different sub-surfaces in different planes with a corresponding predetermined implant angle therebetween, wherein one sub-surface is a lateral sub-surface adapted to at least partly coat a lateral side of the metatarsal head and the predetermined implant angle between the lateral sub-surface and a dorsal sub-surface mainly coating a dorsal side of the metatarsal head is between 90-180°.

According to embodiments of the present invention, a projection length of the lateral flange is about 0-50% of a total projection length of the lateral and the dorsal flange, or preferably 10-40%, or more preferably 20-30%, or more preferably about 25%. The projection lengths are defined in relation to a three-dimensional coordinate system x, y and z, as illustrated in the FIG. 8a-10b. Projection lengths of the lateral flange and the dorsal flange are projected on the x-axis, or in the xy-plane. The projection length of the lateral flange corresponds to an interface between the lateral flange and the metatarsal head surface projected onto the x-axis, or in the xy-plane. Similarly, the projection length of the dorsal flange corresponds to an interface between the dorsal flange and the metatarsal head surface projected onto the x-axis, or in the xy-plane. In other words, the projection length on the x-axis (or in the xy-plane) corresponds to a leg of a right-angle triangle and the interface between the flange and metatarsal head surface to the hypotenuse of the right-angle triangle, i.e. in the yx-plane. The legs of a first and second right angle triangle, i.e. the projection lengths of the lateral and dorsal flange, together constitute the total projection length. According to embodiments, the projection length of the lateral flange is 0-50% of the total projection length and accordingly the projection length of the dorsal flange is 50-100% is of the total projection length. In another embodiment, the projection length of the lateral flange is 25% of the total projection length and accordingly the projection length of the dorsal flange is 75% is of the total projection length.

In embodiments, the implant receiving surfaces on the metatarsal head can be created, e.g. by drilling, milling, and/or sawing the implant receiving surface using a metatarsal preparation guide tool.

In embodiments, the contour curvature of the articulating surface of the metatarsal implant is designed to correspond to the simulated healthy articulating surface of the damaged metatarsal head at the site of diseased cartilage and/or bone and lateral side of bone.

In embodiments, the contour curvature of the articulating surface of the metatarsal implant is selected from a predefined set of predetermined contour curvatures, as the best match to the simulated healthy articulating surface of the damaged metatarsal head and lateral side of the metatarsal head.

In embodiments, the metatarsal implant comprises an implant peg extending from a bone contacting surface of the metatarsal implant, wherein the bone contacting surface and at least a part of a surface area of the implant peg comprises an osseointegrating structure, such as e.g. a lattice structure or a random lattice structure. In embodiments of the present invention, the peg is attached to the bone using bone cement in order to fixate the peg in a recess in the bone. Further, the peg may be screw shaped to allow screwing the peg into the recess of bone and fixating the peg. In other embodiments, the implant peg may be designed for press-fit into a recess in the metatarsal bone. The use of press-fit (where the implant peg is slightly larger than the recess) secures the implant to the implant receiving surface on the metatarsal head. The implant peg may be tapered at the end, for easier insertion into the recess. It is further possible to use bone cement to fixate the peg also when press-fit or being screw-shaped to secure the attachment event further.

In embodiments, the articulating surface of the metatarsal implant comprises a positioning mark. This makes it easier to accomplish the correct rotational positioning of the metatarsal implant during surgery, which is important because the articulating surface of the metatarsal implant will in most situations not be rotationally symmetric. The positioning mark may e.g. be a rotational positioning mark, or an indication of a direction in relation to the anatomy of the joint.

The above-described problem is also addressed by the claimed MTP implant arrangement for repairing damage in an MTP joint of a patient and in particular for repairing a joint affected by osteoarthritic damage and osteophytes.

The MTP implant arrangement preferably comprises a phalangeal implant, comprising an articulating surface, and a metatarsal implant, adapted to be attached to an implant receiving surface which has been created on a metatarsal head of the patient by mechanical preparation of the metatarsal head to create implant receiving surfaces, including a lateral surface, in at least two different planes with a predetermined angle therebetween. A bone contacting surface of the metatarsal implant is designed to correspond to the implant receiving surfaces, the bone contacting surface thus comprising at least two different sub-surfaces in different planes, including a lateral surface, with a corresponding predetermined implant angle therebetween. The articulating surfaces of the phalangeal implant and the metatarsal implant are preferably designed to allow them to interact with each other when the implants are implanted into the metatarsophalangeal joint of the patient. The articulating surface of the metatarsal implant is preferably a metal, metal alloy or ceramic surface, and the articulating surface of the phalangeal implant is preferably not a metal, metal alloy or ceramic surface. This enables the repairing of damage in a metatarsophalangeal joint of a patient with an implant arrangement that avoids a metal-on-metal interface.

Moreover, the above-described problem is also addressed by the claimed MTP implant arrangement for repairing damage in an MTP joint of a patient and in particular for repairing a joint affected by osteoarthritic damage and osteophytes. The included metatarsal implant is adapted to be attached to an implant receiving surface which has been created on a metatarsal head of the patient by mechanical preparation of the metatarsal head and lateral side to create implant receiving surfaces, including a lateral surface, in at least two different planes with a predetermined angle therebetween. A bone contacting surface of the metatarsal implant is designed to correspond to the implant receiving surfaces, the bone contacting surface thus comprising at least two different sub-surfaces in different planes with a corresponding predetermined implant angle therebetween, wherein one sub-surface is a lateral sub-surface adapted to at least partly coat a lateral side of the metatarsal head and the predetermined implant angle between the lateral sub-surface and a dorsal sub-surface mainly coating a dorsal side of the metatarsal head is between 90-180°.

In addition, the above described problem is addressed by the claimed MTP implant arrangement for repairing damage in a MTP joint of a patient and the included metatarsal implant is adapted to be attached to an implant receiving surface which has been created on a metatarsal head of the patient by mechanical preparation of the metatarsal head to create implant receiving surfaces by removing sections of the metatarsal head in at least three different planes by means of drilling, sawing or milling, so that the implant receiving surface becomes asymmetrical, in order to lock the metatarsal implant in a position where it cannot be rotated. A bone contacting surface of the metatarsal implant is designed to correspond to the implant receiving surface, the bone contacting surface thus comprising at least three different sub-surfaces in different planes, and at least one junction point where three sub-surfaces meet.

In embodiments, the articulating surface of the metatarsal implant comprises titanium or titanium alloy, titanium nitride, titanium niobium nitride, and/or a cobalt-chromium alloy. Such materials are very suitable for a metatarsal implant. Such materials also enable highly polished surfaces providing smooth surfaces toward bone and tissue. If the lateral flange is made in such a material and preferably is highly polished, smooth surface can be achieved thereby accommodating full range of motion of the joint and preventing arthrofibrosis In embodiments, the articulating surface of the phalangeal implant comprises a polymer material, such as polyethylene, e.g. the polyethylene UHMWPE (e.g. cross-linked UHMWPE or vitamin E enhanced UHMWPE). This avoids a very hard surface, such as a metal, metal alloy or ceramic surface, interfacing with another very hard surface, creating e.g. a metal-on-metal interface between the implants. The main body of the phalangeal implant may be manufactured from metal, metal alloy or ceramic, but the articulating surface preferably comprises a polymer material, such as polyethylene, e.g. the polyethylene UHMWPE. If the bone contacting surface of the phalangeal implant is a non-porous metal, metal alloy or ceramic surface, it may be advantageous to coat the bone contacting surface with an osseointegrating and/or bioactive material, such as e.g. hydroxy apatite.

The metatarsal implant may be the above-described metatarsal implant, but it may also be a standardized metatarsal implant, selected from a predefined set of standardized metatarsal implants having varying dimensions.

The above referenced MTP joint is preferably a 1st MTP joint, but other MTP joints of a patient are also conceivable.

The scope of the invention is defined by the claims which are incorporated into this section by reference. A more complete understanding of embodiments of the invention will be afforded to those skilled in the art, as well as a realization of additional advantages thereof, by the consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1A:
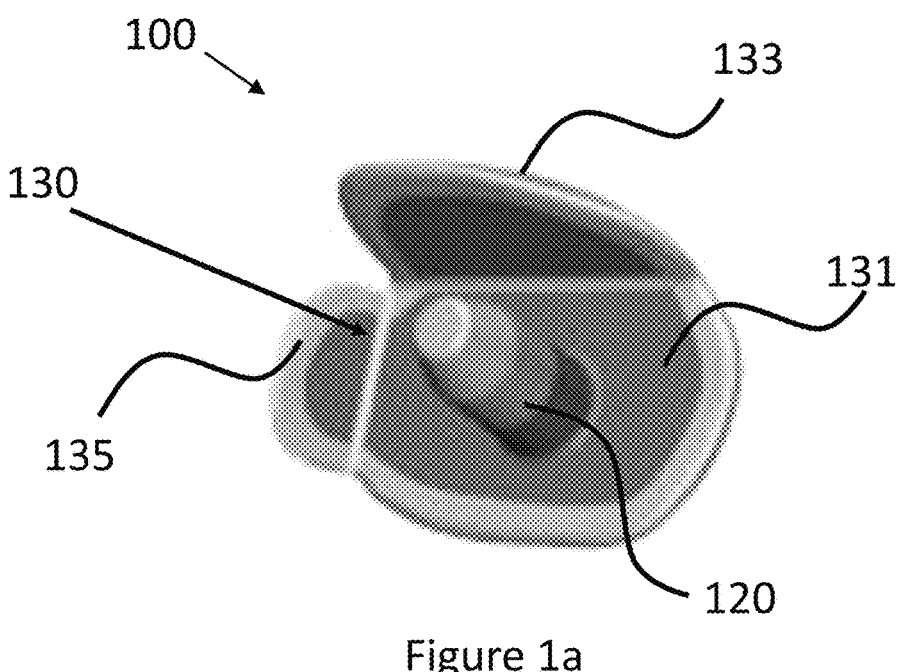
FIGS. 1a-1b illustrate further embodiments of a metatarsal implant, in accordance with one or more embodiments described herein.

Implants for a MTP joint often limit the dorsiflexion of the toe and therefore do not give the patient back a full range of motion. One reason for this is that they do not take full account of the sesamoid bones, which move around the metatarsal head as the toe is bent. Unless the sesamoid gliding path is perfectly smooth, there is always a risk that the sesamoid bones will lock against the implant. Another reason may be that raw bone surfaces after osteophyte/bone spurs removal cause friction in the joint, which may be particularly occurring on a lateral side of the MTP joint. Implants for MTP joints often limit the dorsiflexion of the toe, and therefore often do not give the patient back a full range of motion. One reason for this is that they do not take full account of the sesamoid bones, which move around the metatarsal head as the toe is bent. Another reason may be that raw bone surfaces after osteophyte/bone spurs removal cause friction in the joint, which may be particularly occurring on a lateral side of the MTP joint.

Because of the natural valgus position of the big toe, the forces act asymmetrically on the head, the lateral part being exposed to a higher load. This can result in reactive bone spur (osteophyte) formation and hallux limitus. These reactive spurs occur in the area of most load which is the lateral side of the joint. These osteophytes limit the motion of the joint (hallux limitus).

In case of operative treatment for hallux rigidus these osteophytes must be removed in order to liquidate the restriction of motion.

Removal of these osteophytes results in a raw bone surface. After surgery the toe is immobilized. The capsule, synovium and subcutaneous tissue sticks and gets fixed to this raw bone surface, thereby limiting the future motion of the big toe. This process is called arthrofibrosis.

Therefore, there is a need for improved implants suitable for repairing damage in the toes of a patient and in particular, a toe implant suitable for repairing a joint affected by osteoarthritic damage and osteophytes. This is addressed by the claimed metatarsal implant with lateral flange for repairing damage in a MTP joint of a patient. The metatarsal implant is adapted to be attached to an implant receiving surface which has been created on a metatarsal head of the patient by mechanical preparation of the metatarsal head to create at least one implant receiving surface on a lateral surface, for example by removing parts of the metatarsal head by means of drilling, sawing or milling. Preferably, implant receiving surfaces are created on the metatarsal head, including a lateral surface, in at least two different planes, which in some embodiments may have a predetermined angle therebetween. A lateral flange which covers the raw bone surface will prevent adherence of the joint capsule to the lateral side of the metatarsal bone. A lateral flange on the implant provides a smooth surface to accommodate full range of motion of the joint and prevention of arthrofibrosis. The present disclosure relates generally to implants suitable for repairing damage in the toe of a patient, such as e.g. a big toe, especially damage in an MTP joint and on the lateral side of the joint. A lateral flange which covers the raw bone surface will prevent adherence of the joint capsule to the lateral side of the metatarsal bone. A lateral flange on the implant provides a smooth surface to accommodate full range of motion of the joint and prevention of arthrofibrosis. Embodiments of the disclosed solutions are presented in more detail in connection with the figures.

Figure 1B:
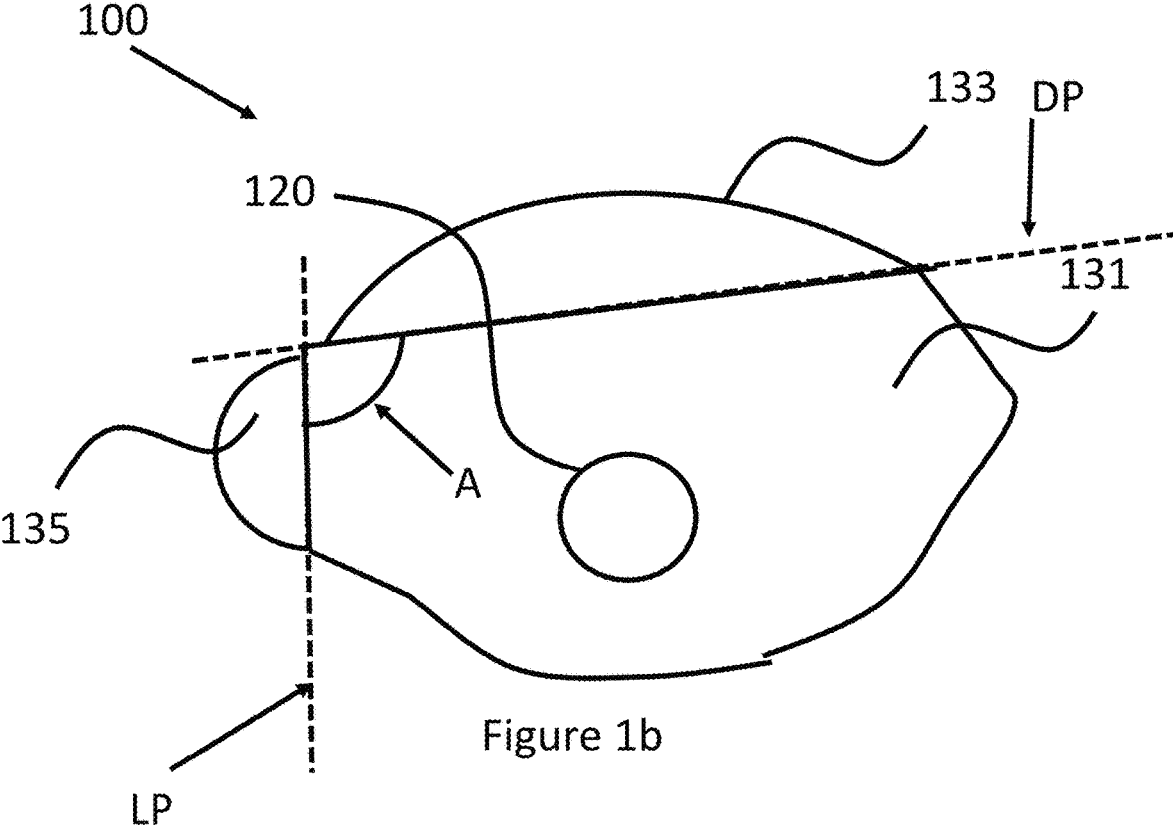
Figure 1C:
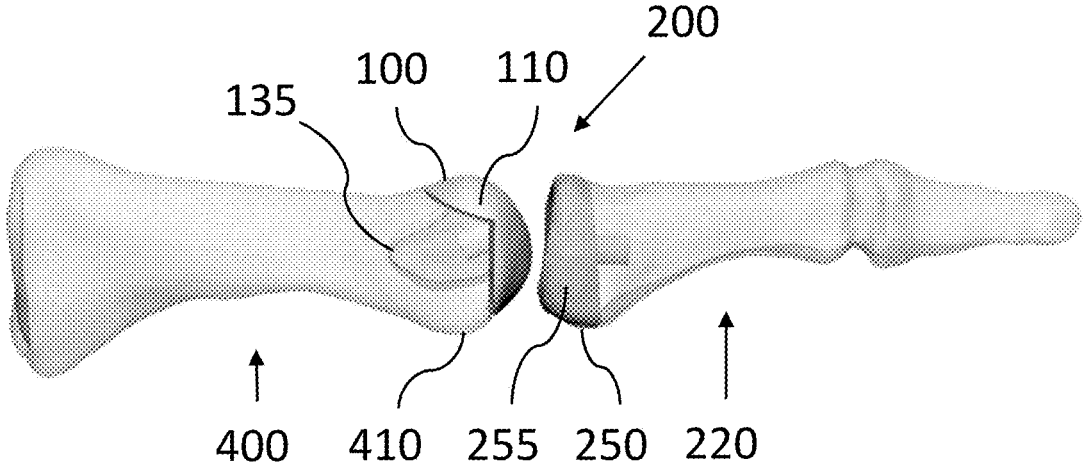
FIG. 1c illustrates an MTP implant arrangement for repairing damage in an MTP joint, in accordance with one or more embodiments described herein.

With reference first to FIGS. 1a-1c, preferred embodiments of the present invention including a lateral flange will be discussed and shown. The metatarsal implant 100 comprises a bone contacting surface 130 shaped to fit an implant receiving surface 420 which has been created on a metatarsal head 410 by mechanical preparation of the metatarsal head 410 to create at least two different planes or surfaces. In the embodiment, shown in FIG. 1a, the bone contacting surface 130 comprises a lateral flange or surface 135, a dorsal flange or sub-surface 133 and a metatarsal head sub-surface 131 in different planes. The lateral sub-surface 135 is adapted to at least partly coat or cover a lateral side of the metatarsal head. The predetermined implant angle A between the lateral sub-surface 135, or a lateral plane LP parallel with the lateral sub-surface 135, and a dorsal sub-surface 133, or a dorsal plane DP parallel with the dorsal sub-surface 131, mainly coating a dorsal side of the metatarsal head is preferably between 90-180°.

The metatarsal implant 100 may be manufactured in a number of different ways, including 3D printing. An articulating surface 110 of the metatarsal implant 100 is preferably a metal, metal alloy or ceramic surface, e.g. comprising titanium (Ti), titanium alloy, titanium nitride (TiN), titanium niobium nitride (TiNbN), and/or a cobalt-chromium (CoCr) alloy. It is preferably polished to a perfectly smooth surface, with a very low surface roughness, to lower the risk of a sesamoid bone locking against the articulating surface 110 of the metatarsal implant 100. The bone contacting surface 130 of the metatarsal implant 100 may be coated with an osseointegrating and/or bioactive material, such as e.g. hydroxy apatite. The bone contacting surface 130 of the metatarsal implant 100 may alternatively be coated with titanium (Ti), titanium alloy, titanium nitride (TiN), or titanium niobium nitride (TiNbN), This reduces the need for using an adhesive for securing the metatarsal implant 100 to the metatarsal head 410, but an adhesive (such as e.g. bone cement) may be used anyhow. The bone contacting surface 130 and at least a part of a surface area of an implant peg 120 preferably comprises an osseointegrating structure (shown in FIGS. 3a-3b as 340), such as e.g. a lattice structure or a random lattice structure. In embodiments of the present invention, the peg is attached to the bone using bone cement in order to fixate the peg in a recess in the bone. Further, the peg 120 may be screw shaped to allow screwing the peg into the recess of bone and fixating the peg. In other embodiments, the implant peg 120 may be designed for press-fit into a recess in the metatarsal bone. The peg 120 of the implant 100 is preferably designed for press-fit into a recess in the bone. The peg 120 of the implant 100 may be tapered at the end, for easier insertion into the recess. If an adhesive such as e.g. bone cement is used, it may not be necessary for the peg 120 to be designed for press-fit into the recess. The use of press-fit (where the implant peg is slightly larger than the recess) secures the implant 100 to the implant receiving surface 420 on the metatarsal head 410 regardless of whether an adhesive such as bone cement is used, but the combination of press-fit and adhesive of course secures the implant 100 even more to the implant receiving surface 420. The implant 100 may comprise one or more recesses for bone cement in the peg, which secures the implant 100 even further.

The bone contacting surface 130 of the metatarsal implant 100 may comprise an osseointegrating structure, such as e.g. a lattice structure or a random lattice structure, in order to improve osseointegration. The osseointegrating structure may comprise any shape of the surface structure that enhances osseointegration, specifically different types of uneven surface structures. The surface structure may e.g. have a grid shape, or an entirely random shape, as long as there are a number of different levels of recesses, regular or irregular, in the surface structure. Such an osseointegrating structure preferably extends also down onto the implant peg 120. In preferred embodiments, at least a part of a surface area of the implant peg 120 comprises such an osseointe-grating structure. However, it is preferred that the osseointegrating structure extends along less than half of the length of the implant peg 120, e.g. along around a third of its length, since it may otherwise be too difficult to remove the metatarsal implant 100 at a later stage. The surface area of the implant peg 120 may also be coated with an osseointegrating and/or bioactive material, such as e.g. hydroxyapatite. The surface area of the implant peg 120 may alternatively be coated with titanium (Ti), titanium alloy, titanium nitride (TiN), or titanium niobium nitride (TiNbN).

The phalangeal implant 250 and/or the metatarsal implant 100 may also comprise a positioning mark (shown in FIG. 2*b*) preferably positioned on the articulating surface 255, 110. This makes it easier to accomplish a correct rotational positioning of the implant during surgery, which may be important because the articulating surface of the implant will in most situations not be rotationally symmetric. The positioning mark 260 (see FIG. 2*b*) may e.g. be a rotational positioning mark, or an indication of a direction in relation to the anatomy of the joint.

The surface curvature of the articulating surface 110 of the metatarsal implant 100 preferably corresponds as closely as possible to a simulated healthy surface curvature of the damaged metatarsal head, and in the embodiment of FIGS. 1*a*-1*b* also extends far enough to always interact with the sesamoid bones, even when the toe is straight. In this way, full account is taken of the sesamoid bones, which move around the metatarsal head as the toe is bent. This increases the possibility of the patient being given back a full range of motion.

By analyzing the surface curvature of the cartilage and/or the bone in a predetermined area comprising and surrounding the site of diseased cartilage, it is possible to simulate a healthy articulating surface of the damaged metatarsal head, generated based on a determined surface curvature of the cartilage and/or the bone in a predetermined area at a site of diseased cartilage and/or bone, to mimic the original, undamaged, articulating surface of the metatarsal head 410. Image data may be analyzed in a data processing system to identify and determine physical parameters for the cartilage and/or bone damage. The physical parameters to be determined may comprise the presence, the location and the size and shape of the cartilage and/or bone damage, as well as curvature of the surface contour of the cartilage or the bone in an area of the cartilage and/or bone damage. This will be described in more detail below with reference to FIG. 9.

When such a healthy articulating metatarsal surface has been simulated, it is possible to design an individualized metatarsal implant 100 with an articulating surface 110 that corresponds to the simulated healthy metatarsal surface.

However, it is also possible to select the best match to the simulated healthy articulating surface of the damaged metatarsal head from a predefined set of predetermined contour curvatures. This enables the use of standardized metatarsal implants 100. In this way, a set of standardized metatarsal implants 100 of different dimensions may be manufactured and stored, to be later used for repairing damage in the metatarsophalangeal joint.

A standardized metatarsal implant 100 may in this case be selected from a predefined set of standardized metatarsal implants 100 having varying dimensions and geometries. The predefined set of standardized metatarsal implants 100 is preferably created by analyzing dimensional data from stored images of the metatarsal head 410 from a large number of different patients. The standardized metatarsal implant 100 should be selected as a standardized metatarsal implant 100 having dimensions that match the shape of the metatarsal head 410 of the patient, thereby making it suitable for repairing the determined damage. A 3D model of the MTP joint, visualizing the determined damage, may be used in order to determine which standardized metatarsal implant 100 is the best fit for the metatarsal head 410 of the patient.

However, even if it is possible to use a standardized metatarsal implant 100, there will always be cases where it cannot be ascertained that a standardized metatarsal implant 100 will really fit the implant receiving surface 420 on the metatarsal head 410 and repair the damage while taking full account of the sesamoid bones. In order to ascertain that the metatarsal implant 100 will really fit the implant receiving surface 420 on the metatarsal head 410, and repair the damage while taking full account of the sesamoid bones, it is necessary to design an individualized metatarsal implant 100 with an articulating surface 110 that corresponds to the simulated healthy metatarsal surface, which may also extend far enough to always interact with the sesamoid bones.

In the same way as for the metatarsal implant 100, the surface curvature of the articulating surface 255 of the phalangeal implant 250 preferably corresponds as closely as possible to the surface curvature of the undamaged proximal phalanges 220.

By analyzing the surface curvature of the cartilage and/or the bone in a predetermined area comprising and surrounding the site of diseased cartilage, it is possible to simulate a healthy articulating surface of the damaged proximal phalanges 220, generated based on a determined surface curvature of the cartilage and/or the bone in a predetermined area at a site of diseased cartilage and/or bone, to mimic the original, undamaged, articulating surface of the proximal phalanges 220. Image data may be analyzed in a data processing system to identify and determine physical parameters for the cartilage and/or bone damage. The physical parameters to be determined may comprise the presence, the location and the size and shape of the cartilage and/or bone damage, as well as curvature of the surface contour of the cartilage or the bone in an area of the cartilage and/or bone damage.

When such a healthy articulating phalangeal surface has been simulated, it is possible to design an individualized phalangeal implant 250 with an articulating surface 255 that corresponds to the simulated healthy phalangeal surface.

However, it is also possible to select the best match to the simulated healthy articulating surface of the damaged proximal phalanges 220 from a predefined set of predetermined contour curvatures. This enables the use of standardized phalangeal implants 250. In this way, a set of standardized phalangeal implants 250 with different dimensions may be manufactured and stored, to be later used for repairing damage in the MTP joint.

A standardized phalangeal implant 250 may in this case be selected from a predefined set of standardized phalangeal implants 250 having varying dimensions. The standardized phalangeal implant 250 should be selected as a standardized phalangeal implant 250 having dimensions that match the shape of the proximal end of the proximal phalanges 220 of the patient, thereby making it suitable for repairing the determined damage. A 3D model of the MTP joint, visualizing the determined damage, may be used in order to determine which standardized phalangeal implant 250 is the best fit for the proximal end of the proximal phalanges 220 of the patient.

However, even if it is possible to use a standardized phalangeal implant 250, there will always be cases where it cannot be ascertained that a standardized phalangeal implant 250 will really fit the implant receiving surface on the proximal phalanges and be designed to interact perfectly with the metatarsal implant 100. In order to ascertain that the phalangeal implant 250 will really fit the implant receiving surface on the proximal phalanges and be designed to interact perfectly with the metatarsal implant 100, it is necessary to design an individualized phalangeal implant 250 with an articulating surface 255 that corresponds to the simulated healthy phalangeal surface.

The metatarsal implant 100 with lateral flange may be used alone, or together with a phalangeal implant 250 in an MTP implant arrangement 200, as discussed below. In such an MTP implant arrangement 200, it is preferred if either both the metatarsal implant 100 and the phalangeal implant 250 are individualized, or both the metatarsal implant 100 and the phalangeal implant 250 are standardized. However, it is also possible to combine an individualized metatarsal implant 100 with a standardized phalangeal implant 250, or a standardized metatarsal implant 100 with an individualized phalangeal implant 250.

A correct rotational positioning of the metatarsal implant 100 is very important because the lateral flange 135 must be placed on the correct site of the metatarsal head 410, i.e. the site of the damage caused by osteofytes, and the articulating surface 110 of the metatarsal implant 100 will in most situations not be rotationally symmetric. An important reason for designing the articulating surface 110 of the metatarsal implant 100 to match the simulated healthy articulating surface of the metatarsal head 410 is to ensure that the metatarsal implant 100 fits smoothly on the metatarsal head 410 and takes full account of the sesamoid bones.

A marking on the cartilage surface makes it easy for the surgeon to attach metatarsal implant 100 to the metatarsal head 410 with a correct rotational positioning if the metatarsal implant 100 also comprises a positioning mark. However, the metatarsal implant 100 may also comprise a positioning mark that is simply an indication of a direction in relation to the anatomy of the joint.

Insert tools may be used to aid the positioning of the metatarsal implant 100 on the implant receiving surface 420 of the metatarsal head 410. It is e.g. possible to use a mandrel as an insert tool, as is commonly known for trochlear implants. There may be a positioning mark on the insert tool, so that the implant engaging portion may be correctly rotated with respect to the metatarsal implant 900.

Figure 2A:
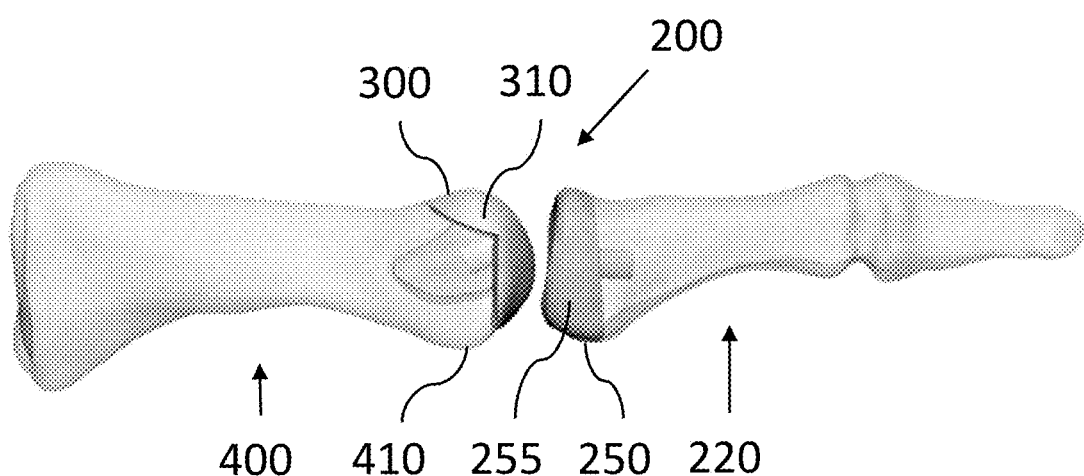
FIGS. 2a-b illustrate an MTP implant arrangement for repairing damage in an MTP joint, in accordance with one or more embodiments described herein.
Figure 2B:
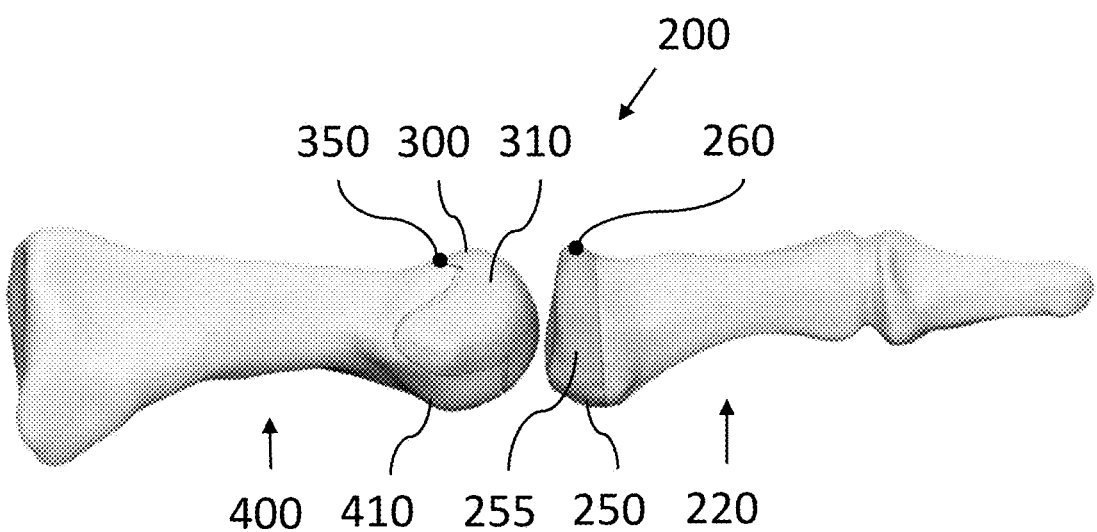

FIGS. 2a-b illustrate an MTP implant arrangement 200 for repairing damage in an MTP joint of a patient, comprising a metatarsal implant 300 and a phalangeal implant 250. Implants 250, 300 are illustrated as implanted into the MTP joint, with the metatarsal implant 300 attached to the metatarsal head 410 and the phalangeal implant 250 attached to the proximal end of the proximal phalanges 220. The implants 250, 300 comprise articulating surfaces 255, 310 that are designed to allow them to interact with each other when the implants 250, 300 are implanted into the MTP joint of the patient.

The mechanical preparation of the implant receiving surfaces on the metatarsal head can be e.g. drilling, milling, and/or sawing the implant receiving surface using a metatarsal preparation guide tool. Since there is often damage on more than one side of the metatarsal head 410, and in particular on the lateral side as discussed above, it may be desirable for the metatarsal implant to be shaped so that it covers different sides of the metatarsal head 410 and in embodiments covers a lateral side and a dorsal surface of the end of the metatarsal head 410. There may e.g. be osteophytes that need to be removed from the metatarsal head 410, and in that case the metatarsal implant 100 or 300 preferably encloses the portions of the metatarsal head 410 where such osteophytes have been removed.

Thus, according to preferred embodiments of the present invention, bone contacting surfaces (see for example 330 of FIGS. 3a-3b and 930 of FIGS. 9a and 9b) of the metatarsal implant 100 and 300 with lateral flange is designed to correspond to implant receiving surfaces 420, the bone contacting surfaces (see for example 130 and 330 in FIGS. 1a-1c and 3a, 3b, respectively) comprising at least two different sub-surfaces in different planes with a predetermined implant angle therebetween, and a contour curvature of an articulating surface of the metatarsal implant is designed by simulating a healthy articulating surface of the damaged metatarsal head, generated based on a determined surface curvature of the cartilage and/or the bone in a predetermined area at a site of diseased cartilage and/or bone, to mimic the original, undamaged, articulating surface of the metatarsal head. At least one of the sub-surfaces is a lateral flange covering a lateral side of the metatarsal head.

The metatarsal implant 300 may be manufactured in a number of different ways, including 3D printing. An articulating surface 310 of the metatarsal implant 300 is preferably a metal, metal alloy or ceramic surface, e.g. comprising titanium (Ti), titanium alloy, titanium nitride (TiN), titanium niobium nitride (TiNbN), and/or a cobalt-chromium (CoCr) alloy. It is preferably polished to a perfectly smooth surface, with a very low surface roughness, to lower the risk of a sesamoid bone locking against the articulating surface 310 of the metatarsal implant 300. The bone contacting surface 330 of the metatarsal implant 300 may be coated with an osseointegrating and/or bioactive material, such as e.g. hydroxyapatite. The bone contacting surface 330 of the metatarsal implant 300 may alternatively be coated with titanium (Ti), titanium alloy, titanium nitride (TiN), or titanium niobium nitride (TiNbN), This reduces the need for using an adhesive for securing the metatarsal implant 300 to the metatarsal head 410, but an adhesive (such as e.g. bone cement) may be used anyhow. Referring now to FIGS. 3a-d, further embodiments of the present invention comprising a metatarsal implant 300 for repairing damage in an MTP joint, such as the 1$^{st}$ MTP joint of a patient are illustrated. The metatarsal implant 300 is preferably adapted to be attached to an implant receiving surface 420 which has been created on a metatarsal head 410 by removing sections of the metatarsal head 410 in at least three different planes by means of drilling, sawing or milling. Since there is often damage on more than one side of the metatarsal head 410, it is often desirable for the metatarsal implant 300 to be shaped so that it encloses the end of the metatarsal head 410 but in particular such that it covers a lateral side of the metatarsal head. There may e.g. be osteophytes that need to be removed from the metatarsal head 410, and in that case the metatarsal implant 300 preferably encloses the portions of the metatarsal head 410 where such osteophytes have been removed.

Figure 3A:
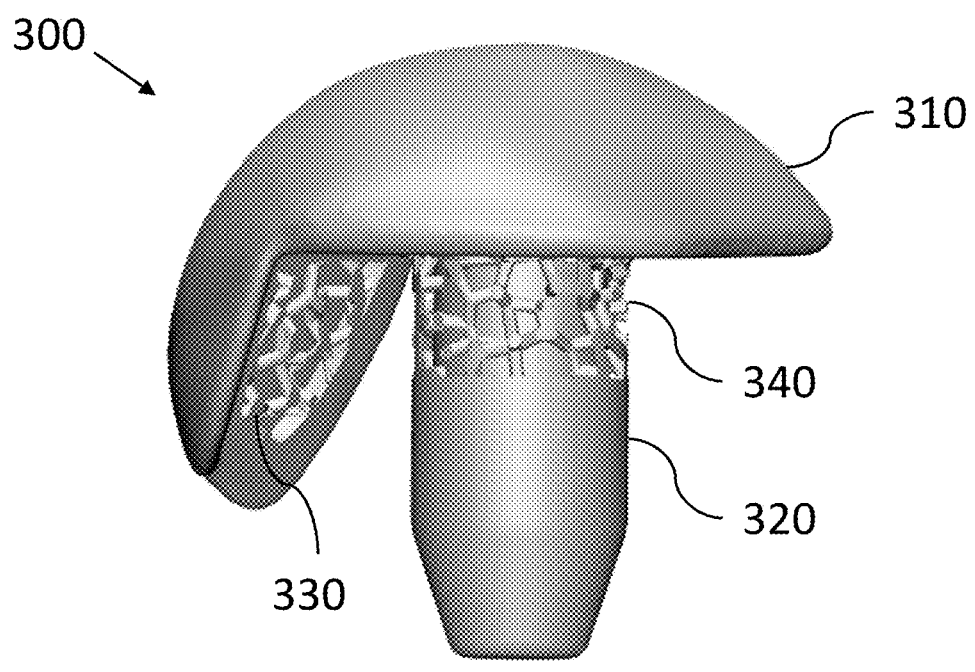
FIGS. 3a-d illustrate embodiments of a metatarsal implant, in accordance with one or more embodiments described herein.
Figure 3B:
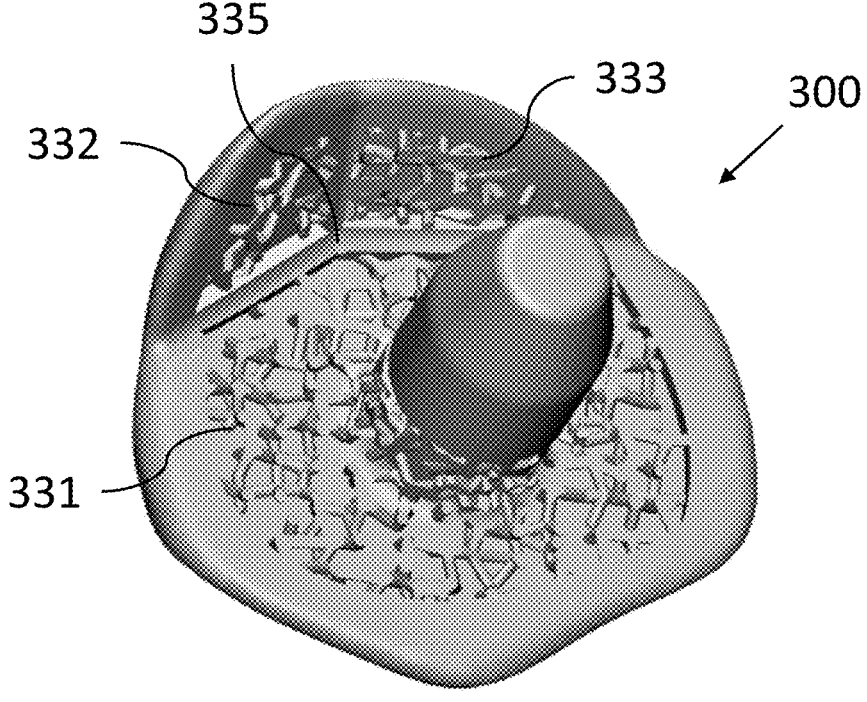
Figure 3C:
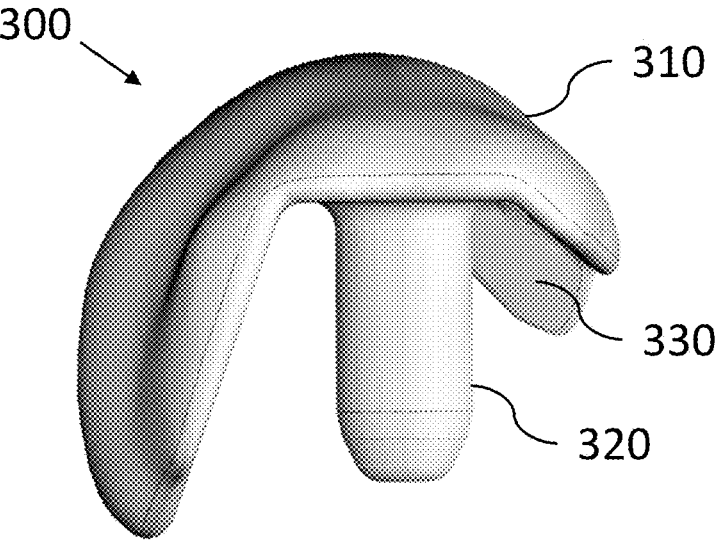

As illustrated in FIGS. 3a-d, the metatarsal implant 300 comprises a bone contacting surface 330 that is shaped to fit an implant receiving surface 420 which has been created on a metatarsal head 410 by removing sections of the metatarsal head 410 in at least three different planes by means of drilling, sawing or milling. This means that the bone contacting surface 330 comprises at least three different sub-surfaces 331, 332, 333, 334 in different planes where at least one coves a lateral side of the metatarsal head, and preferably also at least one junction point 335 where three sub-surfaces 331, 332, 333 meet, as illustrated in FIGS. 3a and 3c. The angle between neighboring sub-surfaces 331, 332, 333, 334 is preferably more than 90°.

The metatarsal implant 300 may be manufactured in a number of different ways, including 3D printing. The articulating surface 310 of the metatarsal implant 300 is preferably a metal, metal alloy or ceramic surface, e.g. comprising titanium (Ti), titanium alloy, titanium nitride (TiN), titanium niobium nitride (TiNbN), and/or a cobalt-chromium (CoCr) alloy. It is preferably polished to a perfectly smooth surface, with a very low surface roughness, to lower the risk of a sesamoid bone locking against the articulating surface 310 of the metatarsal implant 300. The bone contacting surface 330 of the metatarsal implant 300 may be coated with an osseointegrating and/or bioactive material, such as e.g. hydroxyapatite. The bone contacting surface 330 of the metatarsal implant 300 may alternatively be coated with titanium (Ti), titanium alloy, titanium nitride (TiN), or titanium niobium nitride (TiNbN), This reduces the need for using an adhesive for securing the metatarsal implant 300 to the metatarsal head 410, but an adhesive (such as e.g. bone cement) may be used anyhow. In order to avoid a very hard surface, such as a metal, metal alloy or ceramic surface, interfacing with another very hard surface, creating e.g. a metal-on-metal interface, the phalangeal implant 250 preferably has an articulating surface 255 that is not a metal, metal alloy or ceramic surface. The articulating surface 255 of the phalangeal implant 250 is preferably a polymer surface, e.g. a surface of polyethylene, e.g. the polyethylene UHMWPE (e.g. cross-linked UHMWPE or vitamin E enhanced UHMWPE). Preferably, the whole phalangeal implant 250 is manufactured from the same polymer material, since this simplifies the manufacturing process.

The main body of the phalangeal implant 250 may be manufactured from metal, metal alloy or ceramic, but the articulating surface 255 preferably comprises a polymer material, such as polyethylene, e.g. the polyethylene UHMWPE. If the bone contacting surface of the phalangeal implant 250 is a non-porous metal, metal alloy or ceramic surface, comprising e.g. titanium (Ti) or titanium alloy, titanium nitride (TiN), titanium niobium nitride (TiNbN), and/or a cobalt-chromium (CoCr) alloy, it may be advantageous to coat the bone contacting surface with an osseointegrating and/or bioactive material, such as e.g. hydroxyapatite. The bone contacting surface 330 of the metatarsal implant 300 may alternatively be coated with titanium (Ti), titanium alloy, titanium nitride (TiN), or titanium niobium nitride (TiNbN), This reduces the need for using an adhesive for securing the phalangeal implant 250 to the proximal phalanges 220, but an adhesive (such as e.g. bone cement) may be used anyhow.

The metatarsal implant preferably has an implant peg 320 extending from a bone contacting surface 330, and the phalangeal implant 250 preferably also has an implant peg extending from a bone contacting surface. The bone contacting surface 330 and at least a part of the surface area of the implant peg 320 preferably comprises an osseointegrating structure 340, such as e.g. a lattice structure or a random lattice structure. The pegs of the implants 250, 300 are preferably designed for press-fit into recesses in the bone. The pegs of one or both implants 250, 300 may be tapered at the end, for easier insertion into the recess. If an adhesive such as e.g. bone cement is used, it may not be necessary for the peg of the implant 250, 300 to be designed for press-fit into the recess. The use of press-fit (where the implant peg is slightly larger than the recess) secures the implant 250, 300 to the implant receiving surface 420 on the metatarsal head 410 regardless of whether an adhesive such as bone cement is used, but the combination of press-fit and adhesive of course secures the implant 250, 300 even more to the implant receiving surface 420. One or both implants 250, 300 may comprise one or more recesses for bone cement in the peg, which secures the implant 250, 300 even further.

As illustrated in FIGS. 3a-b, the bone contacting surface 330 of the metatarsal implant 300 may comprise an osseointegrating structure 340, such as e.g. a lattice structure or a random lattice structure, in order to improve osseointegration. The osseointegrating structure may comprise any shape of the surface structure that enhances osseointegration, specifically different types of uneven surface structures. The surface structure may e.g. have a grid shape, or an entirely random shape, as long as there are a number of different levels of recesses, regular or irregular, in the surface structure.

Such an osseointegrating structure 340 preferably extends also down onto the implant peg 320. In preferred embodiments, at least a part of a surface area of the implant peg 320 comprises an osseointegrating structure 340. However, it is preferred that the osseointegrating structure 340 extends along less than half of the length of the implant peg 320, e.g. along around a third of its length, since it may otherwise be too difficult to remove the metatarsal implant 300 at a later stage. The surface area of the implant peg 320 may also be coated with an osseointegrating and/or bioactive material, such as e.g. hydroxyapatite. The surface area of implant peg 320 may alternatively be coated with titanium (Ti), titanium alloy, titanium nitride (TiN), or titanium niobium nitride (TiNbN).

The phalangeal implant 250 and/or the metatarsal implant 300 may also comprise a positioning mark 260, 350, preferably positioned on the articulating surface 255, 310. This makes it easier to accomplish a correct rotational positioning of the implant during surgery, which may be important because the articulating surface of the implant will in most situations not be rotationally symmetric. The positioning mark 260 may e.g. be a rotational positioning mark, or an indication of a direction in relation to the anatomy of the joint.

Figure 3D:
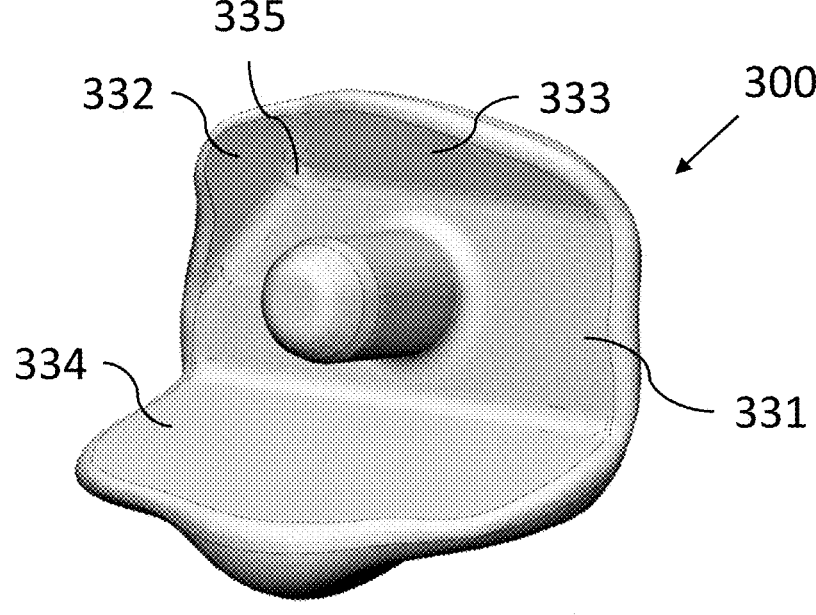

The surface curvature of the articulating surface 310 of the metatarsal implant 300 preferably corresponds as closely as possible to a simulated healthy surface curvature of the damaged metatarsal head 410, and in the embodiment of FIGS. 3c-d also extends far enough to always interact with the sesamoid bones, even when the toe is straight. In this way, full account is taken of the sesamoid bones, which move around the metatarsal head as the toe is bent. This increases the possibility of the patient being given back a full range of motion.

By analyzing the surface curvature of the cartilage and/or the bone in a predetermined area comprising and surrounding the site of diseased cartilage, it is possible to simulate a healthy articulating surface of the damaged metatarsal head 410, generated based on a determined surface curvature of the cartilage and/or the bone in a predetermined area at a site of diseased cartilage and/or bone, to mimic the original, undamaged, articulating surface of the metatarsal head 410. The image data may be analyzed in a data processing system to identify and determine physical parameters for the cartilage and/or bone damage. The physical parameters to be determined may comprise the presence, the location and the size and shape of the cartilage and/or bone damage, as well as curvature of the surface contour of the cartilage or the bone in an area of the cartilage and/or bone damage.

When such a healthy articulating metatarsal surface has been simulated, it is possible to design an individualized metatarsal implant 300 with an articulating surface 310 that corresponds to the simulated healthy metatarsal surface.

However, it is also possible to select the best match to the simulated healthy articulating surface of the damaged metatarsal head 410 from a predefined set of predetermined contour curvatures. This enables the use of standardized metatarsal implants 300. In this way, a set of standardized metatarsal implants 300 of different dimensions may be manufactured and stored, to be later used for repairing damage in the MTP joint A standardized metatarsal implant 300 may in this case be selected from a predefined set of standardized metatarsal implants 300 having varying dimensions. The predefined set of standardized metatarsal implants 300 is preferably created by analyzing dimensional data from stored images of the metatarsal head 410 from a large number of different patients. The standardized metatarsal implant 300 should be selected as a standardized metatarsal implant 300 having dimensions that match the shape of the metatarsal head 410 of the patient, thereby making it suitable for repairing the determined damage. A 3D model of the MTP joint, visualizing the determined damage, may be used in order to determine which standardized metatarsal implant 300 is the best fit for the metatarsal head 410 of the patient.

However, even if it is possible to use a standardized metatarsal implant 300, there will always be cases where it cannot be ascertained that a standardized metatarsal implant 300 will really fit the implant receiving surface 420 on the metatarsal head 410 and repair the damage while taking full account of the sesamoid bones. In order to ascertain that the metatarsal implant 300 will really fit the implant receiving surface 420 on the metatarsal head 410 and repair the damage while taking full account of the sesamoid bones, it is necessary to design an individualized metatarsal implant 300 with an articulating surface 310 that corresponds to the simulated healthy metatarsal surface, which may also extend far enough to always interact with the sesamoid bones.

In the same way as for the metatarsal implant 310, the surface curvature of the articulating surface 255 of the phalangeal implant 250 preferably corresponds as closely as possible to the surface curvature of the undamaged proximal phalanges 220.

By analyzing the surface curvature of the cartilage and/or the bone in a predetermined area comprising and surrounding the site of diseased cartilage, it is possible to simulate a healthy articulating surface of the damaged proximal phalanges 220, generated based on a determined surface curvature of the cartilage and/or the bone in a predetermined area at a site of diseased cartilage and/or bone, to mimic the original, undamaged, articulating surface of the proximal phalanges 220. The image data may be analyzed in a data processing system to identify and determine physical parameters for the cartilage and/or bone damage. The physical parameters to be determined may comprise the presence, the location and the size and shape of the cartilage and/or bone damage, as well as curvature of the surface contour of the cartilage or the bone in an area of the cartilage and/or bone damage.

When such a healthy articulating metatarsal surface has been simulated, it is possible to design an individualized phalangeal implant 250 with an articulating surface 255 that corresponds to the simulated healthy phalangeal surface.

However, it is also possible to select the best match to the simulated healthy articulating surface of the damaged proximal phalanges 220 from a predefined set of predetermined contour curvatures. This enables the use of standardized phalangeal implants 250. In this way, a set of standardized phalangeal implants 250 of different dimensions may be manufactured and stored, to be later used for repairing damage in the MTP joint.

A standardized phalangeal implant 250 may in this case be selected from a predefined set of standardized phalangeal implants 250 having varying dimensions. The standardized phalangeal implant 250 should be selected as a standardized phalangeal implant 250 having dimensions that match the shape of the proximal end of the proximal phalanges 220 of the patient, thereby making it suitable for repairing the determined damage. A 3D model of the MTP joint, visualizing the determined damage, may be used in order to determine which standardized phalangeal implant 250 is the best fit for the proximal end of the proximal phalanges 220 of the patient.

However, even if it is possible to use a standardized phalangeal implant 250, there will always be cases where it cannot be ascertained that a standardized phalangeal implant 250 will really fit the implant receiving surface on the proximal phalanges and be designed to interact perfectly with the metatarsal implant 300. In order to ascertain that the phalangeal implant 250 will really fit the implant receiving surface on the proximal phalanges and be designed to interact perfectly with the metatarsal implant 300, it is necessary to design an individualized phalangeal implant 250 with an articulating surface 255 that corresponds to the simulated healthy phalangeal surface.

The metatarsal implant 300 may be used alone, or together with a phalangeal implant 250 in an MTP implant arrangement 200, as illustrated in FIGS. 2*a-b*. In such an MTP implant arrangement 200, it is preferred if either both the metatarsal implant 300 and the phalangeal implant 250 are individualized, or both the metatarsal implant 300 and the phalangeal implant 250 are standardized. However, it is also possible to combine an individualized metatarsal implant 300 with a standardized phalangeal implant 250, or a standardized metatarsal implant 300 with an individualized phalangeal implant 250.

Figure 4A:
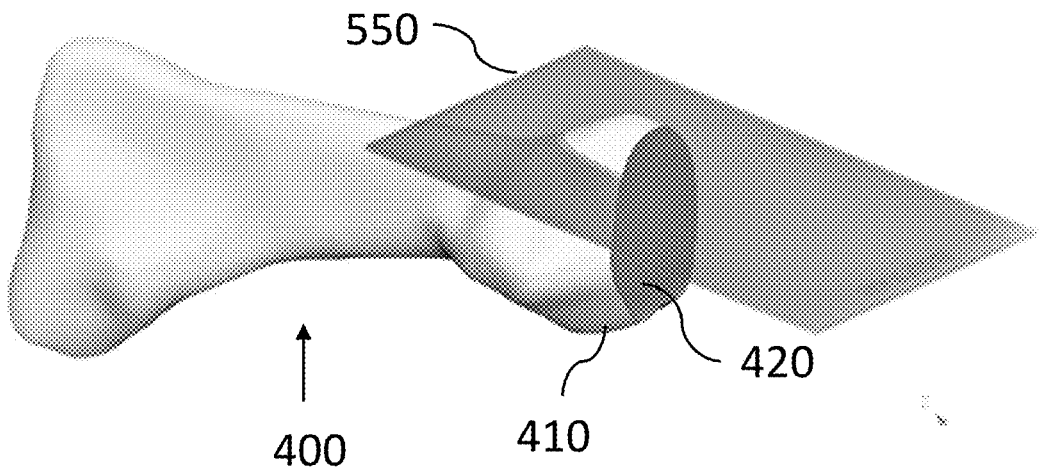
FIGS. 4a-b illustrate the creation of an implant receiving surface suitable for receiving a metatarsal implant on a metatarsal head, in accordance with one or more embodiments described herein.
Figure 4B:
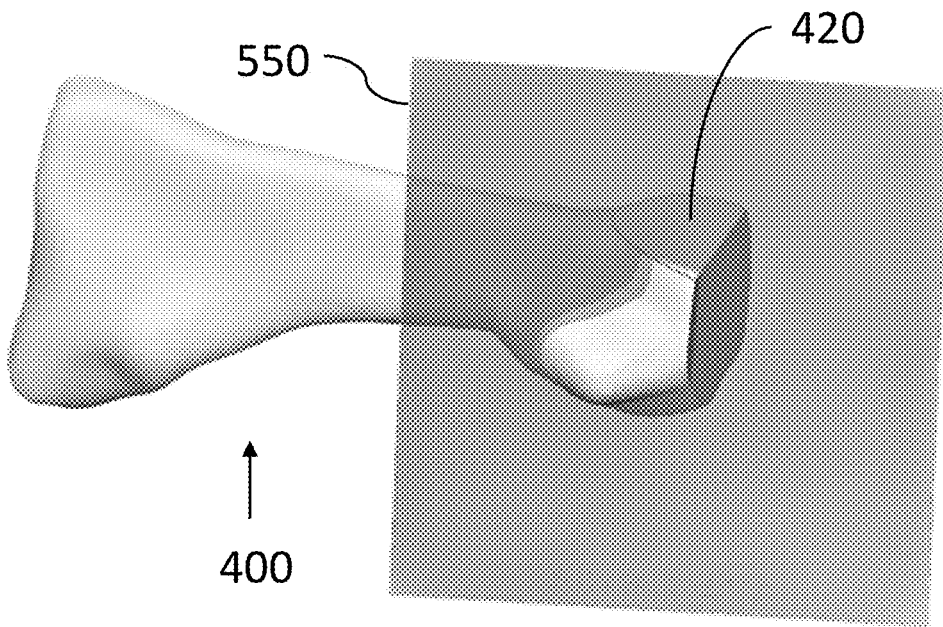
Figure 4C:
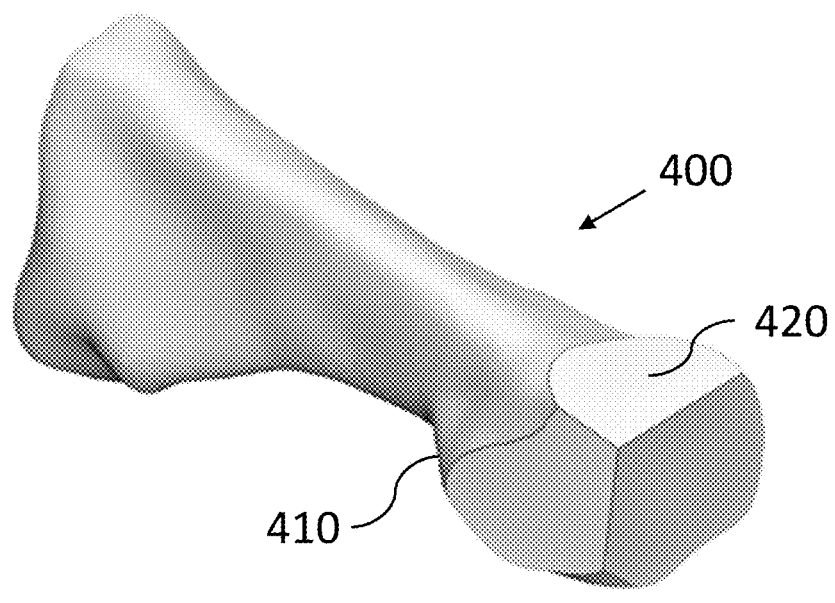
FIG. 4c illustrates a metatarsal bone comprising an implant receiving surface suitable for receiving a metatarsal implant on a metatarsal head, in accordance with one or more embodiments described herein.
Figure 4D:
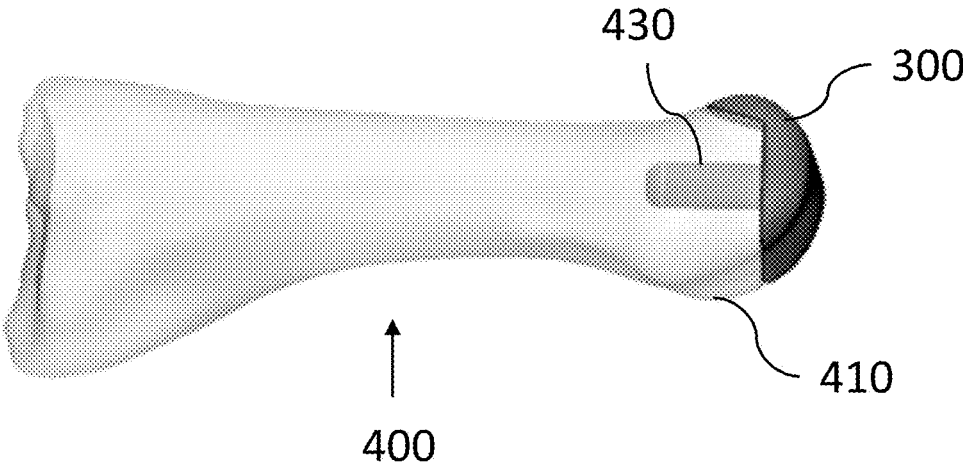
FIGS. 4d-e illustrate embodiments of a metatarsal implant positioned on a metatarsal head, in accordance with one or more embodiments described herein.
Figure 4E:
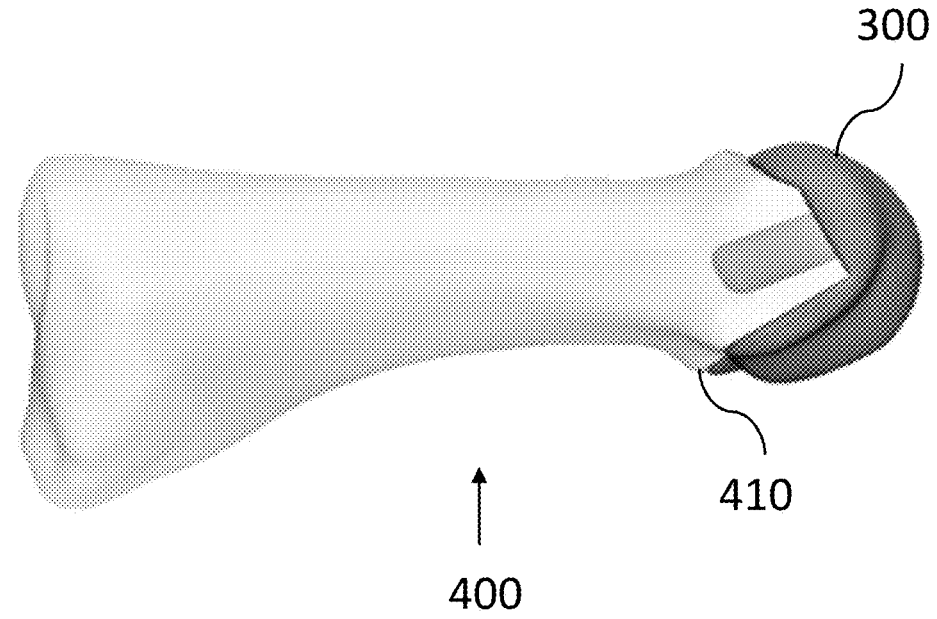

FIGS. 4*a-b* illustrate the creation of an implant receiving surface 420 suitable for receiving a metatarsal implant 300 on a metatarsal head 410 by removing sections of the metatarsal head 410 in at least three different planes including at least one on the lateral side of the metatarsal head by means of drilling, sawing or milling, FIG. 4*c* illustrates a metatarsal bone 400 comprising an implant receiving surface 420 suitable for receiving a metatarsal implant 300 on a metatarsal head 410, and FIGS. 4*d-e* illustrate embodiments of a metatarsal implant 300 positioned on a metatarsal head 410.

According to embodiments of the present invention, a metatarsal surgical kit (kit of surgical instruments) is provided. The metatarsal surgical kit preferably comprises: a metatarsal implant 100 or 300 comprising a lateral flange; at least one metatarsal preparation guide tool for preparing sections of the metatarsal head in at least two different implant receiving surfaces, including a lateral surface, with a predetermined angle therebetween, a metatarsal preparation guide tool comprising a contact surface configured to have a shape and contour that is designed to correspond to and to fit the actual contour of the metatarsal bone in a predetermined area of the metatarsal bone; and a metatarsal drill guide tool for drilling a recess for an implant peg extending from a bone contacting surface of the metatarsal implant, the metatarsal drill guide tool comprising a contact surface configured to have a shape and contour that is designed to correspond to and to fit the implant receiving surface on the metatarsal head, the contact surface comprising at least two different sub-surfaces, including a lateral surface, in different planes with a predetermined implant angle therebetween.

Figure 5:
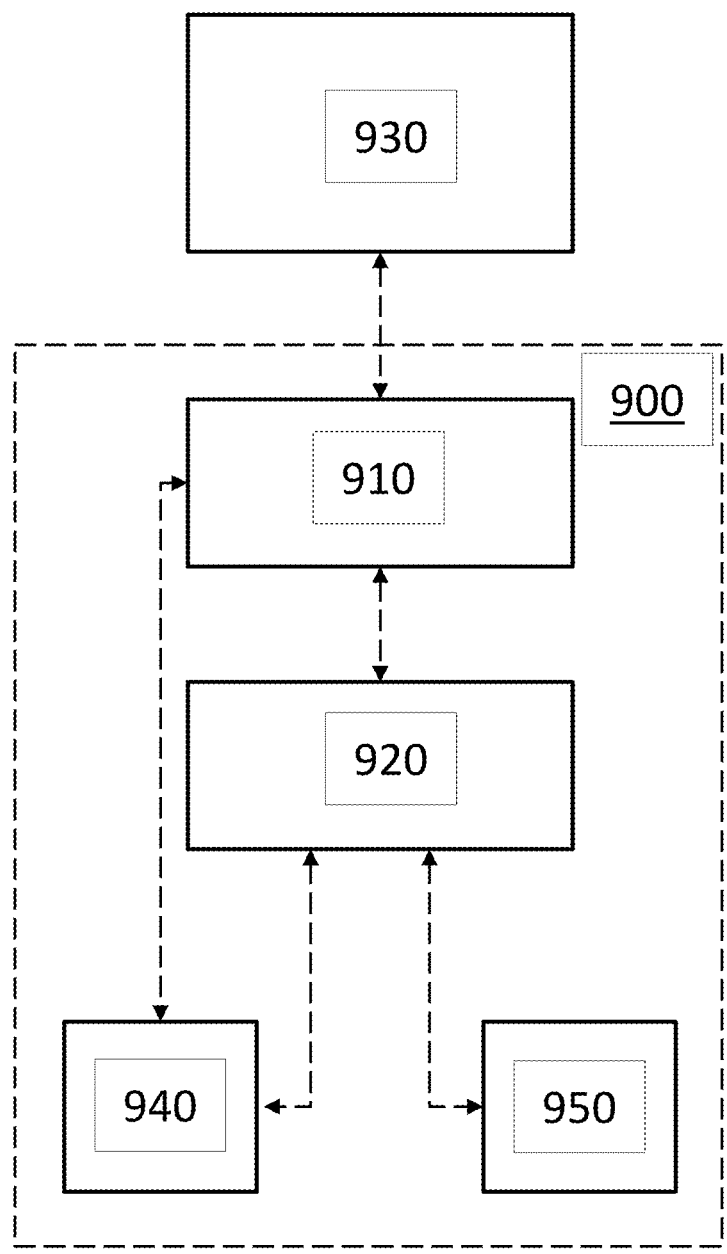
FIG. 5 shows a schematic view of a system for customizing a metatarsal implant, in accordance with one or more embodiments described herein.
Figure 6:
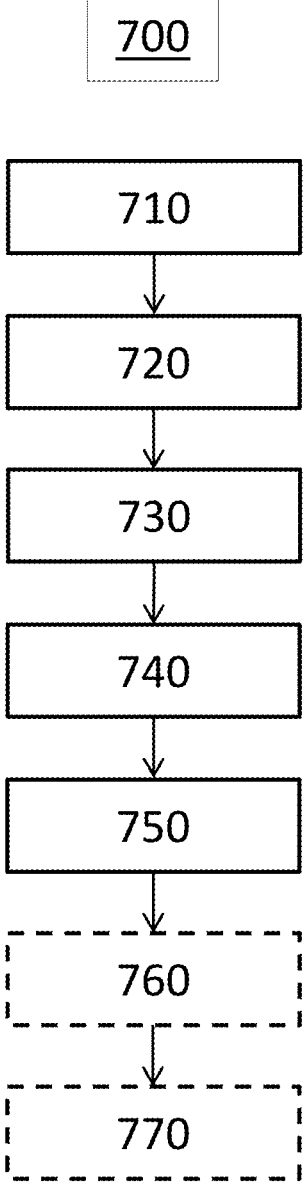
FIG. 6 is a schematic flow diagram for a method for customizing a metatarsal implant, in accordance with one or more embodiments described herein.

FIG. 5 shows a schematic view of system 900 for customizing a metatarsal implant for repairing damage in an MTP joint of a patient. The metatarsal implant is adapted to be attached to an implant receiving surface which has been created on a metatarsal head of the patient by mechanical preparation of the metatarsal head to create implant receiving surfaces, including a lateral surface, in at least two different planes with a predetermined angle therebetween. The metatarsal implant 100 and 300 comprising a lateral flange is according to the invention adapted to be attached to implant receiving surfaces (see for example 420 in FIGS. 4a-4c) which has been created on a metatarsal head (see for example 410 in FIGS. 4a-4c) of the patient by mechanical preparation where at least two implant receiving surfaces have been created with a predetermined angle therebetween. In preferred embodiments of the present invention, the metatarsal implant includes a lateral flange, covering wholly or partly a lateral side of the metatarsal head. A metatarsal implant 100 or 300 with lateral flange according to the present invention has been discussed above with reference to, for example, FIGS. 1a-1c and FIGS. 3a-3d.

In a further embodiment, the implant receiving surfaces has been created on a metatarsal head of a patient by removing sections of the metatarsal head in at least three different planes by means of drilling, sawing or milling. According to embodiments, the system 900 comprises a display 940, at least one manipulation tool 950, and a storage media 910, configured to receive and store image data and parameters. In some embodiments, the system 900 is communicatively coupled to a medical imaging system 930. The medical imaging system 930 may be configured to capture or generate medical images, e.g. radiology images such as X-ray images, ultrasound images, computed tomography (CT), e.g. CBCT, images, nuclear medicine including positron emission tomography (PET) images, and magnetic resonance imaging (MRI) images. The storage media 910 may be configured to receive and store medical images from the medical imaging system 930. In embodiments, medical images are uploaded into the storage media 910 by personnel at a medical care facility, preferably the medical care facility where the medical imaging takes place. Medical images may however also be uploaded into storage media 910 by another medical care facility, or by other authorized personnel. The uploading of medical images may also be an automatic uploading directly from one system to another.

In one or more embodiments, the system 900 comprises at least one processor 920 configured to: obtain a three-dimensional image representation of an MTP joint of a patient based on medical images generated using a medical imaging system 930; determine damage to the metatarsal head of the patient by analyzing medical images generated using a medical imaging system 930; design a bone contacting surface of the metatarsal implant to correspond to the implant receiving surface. A bone contacting surface of the metatarsal implant is designed to correspond to the implant receiving surfaces, the bone contacting surface comprising at least two different sub-surfaces, including a lateral surface, in different planes with a corresponding predetermined implant angle therebetween. In a further embodiment, the bone contacting surface comprising at least three different sub-surfaces in different planes, and at least one junction point where three sub-surfaces meet; and design a contour curvature of an articulating surface of the metatarsal implant, using said three-dimensional image representation of the MTP joint, by simulating a healthy articulating surface of the damaged metatarsal head based on the determined surface curvature of the cartilage and/or the bone in a predetermined area at the site of diseased cartilage and/or bone, to mimic the original, undamaged, articulating surface of the metatarsal head.

In one or more embodiments, the at least one processor 920 is configured to design the contour curvature of the articulating surface of the metatarsal implant 100 or 300 comprising a lateral flange to correspond to the curvature of the simulated healthy articulating surface of the damaged metatarsal head. The design of the contour curvature of the articulating surface of the metatarsal implant 100 or 300 comprising a lateral flange preferably involves designing a contour curvature that corresponds to a 3D image of a simulated healthy cartilage surface.

In one or more embodiments, the at least one processor 920 is configured to select the contour curvature of the articulating surface from a predefined set of predetermined contour curvatures, as the best match to the simulated healthy articulating surface of the damaged metatarsal head.

In embodiments, at least one processor 920 is configured to also output the shape and dimensions of the customized metatarsal implant 100 or 300 as parameters for manufacturing said customized metatarsal implant 100 and 300.

The at least one processor 920 may for example be a general data processor, or other circuit or integrated circuit capable of executing instructions to perform various processing operations. The at least one processor 920 may in some embodiments comprise several different processors 920 which together perform the claimed functions. In the same way, the storage media 910 may in some embodiments comprise several different storage media 110 which together perform the claimed functions.

The display 940 may be configured to receive image data for display via the processor 920, and/or to retrieve image data for display directly from the storage media 910, possibly in response to a control signal received from the processor 920 or the at least one manipulation tool 950.

The processor 120 may further be configured to perform any or all of the method steps of any or all of the embodiments presented herein.

Figure 7:
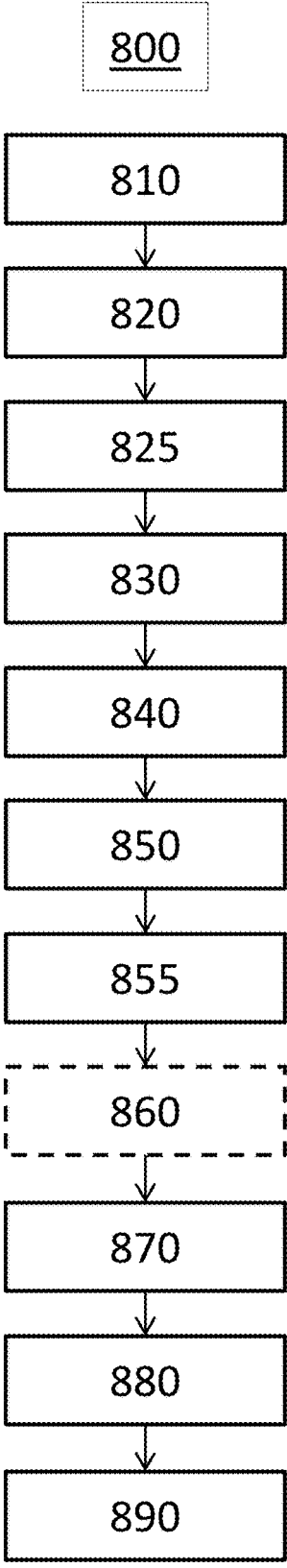
FIG. 7 is a schematic flow diagram for a method for attaching a metatarsal implant to a metatarsal head, in accordance with one or more embodiments described herein.

FIG. 7 is a flow diagram of embodiments of a method 700 for customizing a metatarsal implant 100 or 300 comprising a lateral flange for repairing damage in an MTP joint of a patient, the metatarsal implant 100 or 300 being adapted to be attached to an implant receiving surface 420 which has been created on a metatarsal head 410 of the patient by mechanical preparation of the metatarsal head 410 in at least two different planes. In accordance with one or more embodiments, the method 700 comprises:

Step 710: obtaining a three-dimensional image representation of the metatarsal head 410 based on medical images generated using a medical imaging system 930.

Step 720: determining damage to the metatarsal head 410 by analyzing medical images generated using a medical imaging system 930.

Step 730: designing a bone contacting surface 130, 330 of the metatarsal implant 100, 300 to correspond to the implant receiving surface 420, the bone contacting surface 130, 330 thus comprising different sub-surfaces in different planes wherein at least one covers a lateral side of the metatarsal head, i.e. comprises a lateral flange.

Step 740: designing a contour curvature of an articulating surface 110, 310 of the metatarsal implant 100, 300, using said three-dimensional image representation of the MTP joint.

Step 750: simulating a healthy articulating surface of the damaged metatarsal head 410 based on a determined surface curvature of the cartilage and/or the bone in a predetermined area at the site of diseased cartilage and/or bone, to mimic the original, undamaged, articulating surface of the metatarsal head 410.

This enables the customizing of a metatarsal implant that takes full account of the sesamoid bones and may also extend far enough to always interact with the sesamoid bones, even when the toe is straight. The MTP joint is preferably the 1$^{st}$ MTP joint, but other MTP joints of a patient are also conceivable.

In embodiments, the designing 740 of the contour curvature of the articulating surface 110, 310 of the metatarsal implants 100, 300 involves one of the following:

Step 760: designing the contour curvature to correspond to the curvature of the simulated healthy articulating surface of the damaged metatarsal head 410.

Step 770: selecting the contour curvature of the articulating surface 110, 310 from a predefined set of predetermined contour curvatures, as the best match to the simulated healthy articulating surface of the damaged metatarsal head 410.

FIG. 8 is a flow diagram of embodiments of a method for attaching a metatarsal implant 100, 300 to an implant receiving surface 420 which has been created on a metatarsal head 410 by mechanical preparation of the metatarsal head 410 in different planes, for repairing damage in an MTP joint of a patient. In accordance with one or more embodiments, the method 800 comprises:

Step 810: attaching at least one metatarsal preparation guide tool to the metatarsal bone 400, the at least one metatarsal preparation guide tool comprising a contact surface configured to have a shape and contour that is designed to correspond to and to fit the actual contour of the metatarsal bone 400 in a predetermined area of the metatarsal bone 400.

Step 820: creating an implant receiving surface 420 on the metatarsal head 410 by mechanically preparing by means of drilling, milling, and/or sawing the implant receiving surface using the metatarsal preparation guide tool and a preparation tool.

Step 825: removing the at least one metatarsal preparation guide tool from the metatarsal bone 400.

Step 830: using a metatarsal implant dummy for verifying that the implant receiving surface 420 has the correct size and shape for receiving the metatarsal implant 300.

Step 840: attaching a metatarsal drill guide tool to the metatarsal bone 400, the metatarsal drill guide tool comprising a contact surface configured to have a shape and contour that is designed to correspond to and to fit the implant receiving surface 420 on the metatarsal head 410, the contact surface thus comprising at least three different sub-surfaces in different planes, and preferably also at least one junction point where three sub-surfaces meet.

Step 850: drilling a recess for an implant peg 120, 320 extending from a bone contacting surface 130, 330 of the metatarsal implant 100, 300.

Step 855: removing the metatarsal drill guide tool from the metatarsal bone 400.

Step 870: placing the metatarsal implant 300 on the implant receiving surface 420.

Step 880: pressing the metatarsal implant 100, 300 to the implant receiving surface 420 using an insert tool.

Step 890: removing the insert tool.

The MTP joint is preferably the 1$^{st}$ MTP joint, but other MTP joints of a patient are also conceivable.

In embodiments, the method 800 further comprises:

Step 860: applying an adhesive, such as e.g. bone cement, on the implant receiving surface 420, and/or on a bone contacting surface 130, 330 of the metatarsal implant 100, 300, before placing the metatarsal implant 100, 300 on the implant receiving surface 420.

In embodiments, the method 800 further comprises making a marking on the cartilage at the side of the implant receiving surface 420 on the metatarsal head 410, in order to ensure a correct rotational positioning of the implant.

Turning now to FIGS. 8a-10b, further embodiments of the present invention will be discussed. Generally, the embodiments will be discussed in relation to a three-dimensional coordinate system x, y and z, as illustrated in the figures. Projection lengths A and B and w are projected on the x-axis, or in the xy-plane. Angle C is defined in the xy-plane and angle D in the yz-plane.

Figure 8A:
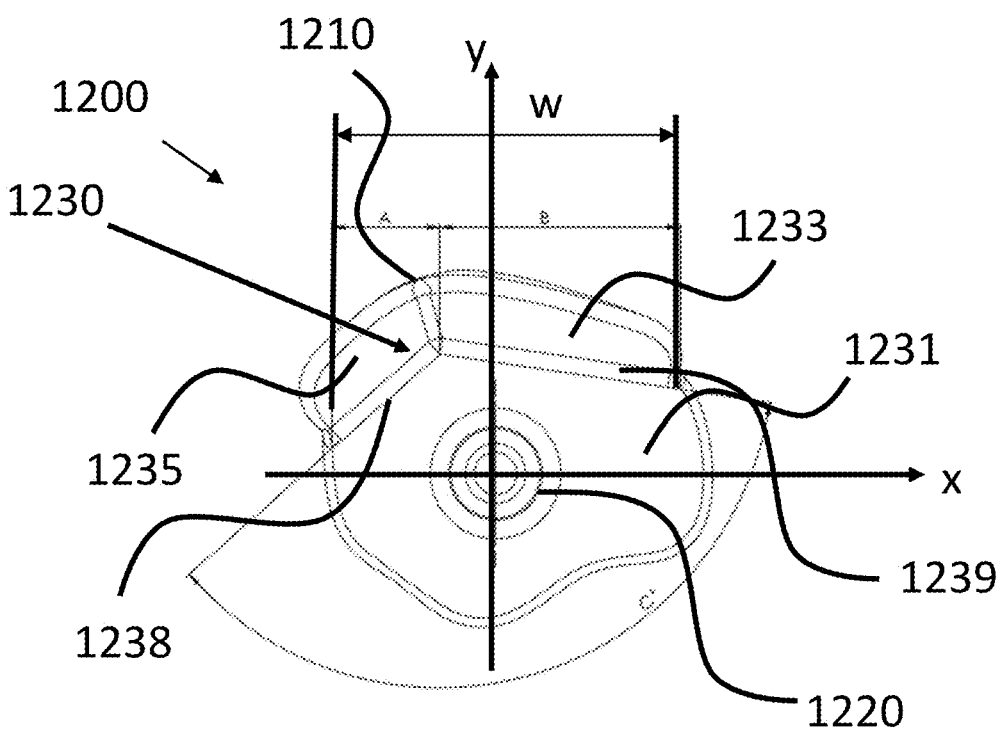
FIGS. 8a-8b illustrate further embodiments of a metatarsal implant, in accordance with one or more embodiments described herein.
Figure 8B:
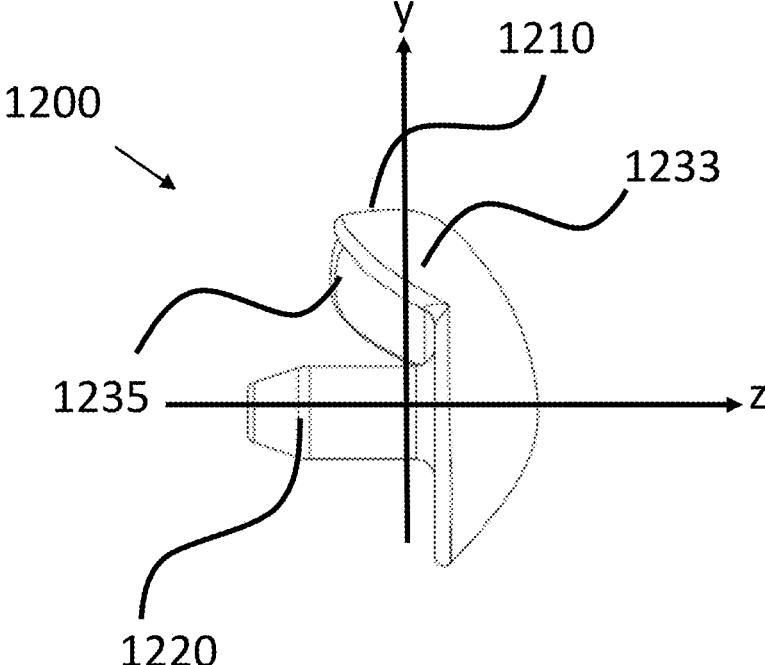

With reference now to FIGS. 8a-8b, preferred embodiments of the present invention including a lateral flange will be discussed and shown. The metatarsal implant 1200 comprises a bone contacting surface 1230 shaped to fit an implant receiving surface which has been created on a metatarsal head by mechanical preparation of the metatarsal head to create at least two different planes or surfaces. In the embodiment, shown in FIG. 8a, the bone contacting surface 1230 comprises a lateral flange or surface 1235, a dorsal flange or surface 1233 and a metatarsal head surface 1231 in different planes. The lateral surface or flange 1235 is adapted to at least partly coat or cover a lateral side of the metatarsal head and the dorsal flange 1233 is adapted to at least partly coat the dorsal side of the metatarsal head. The predetermined implant angle C, in the yx-plane, between the lateral flange 1235 and a dorsal flange 1233 mainly coating a dorsal side of the metatarsal head is preferably between 90-180°.

Figure 10A:
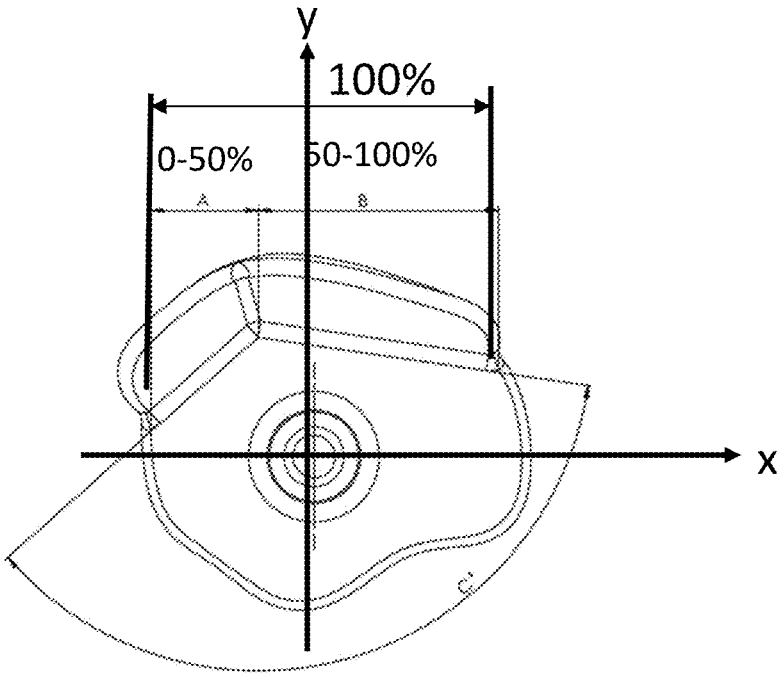
FIGS. 10a-10b illustrate details of embodiments of a metatarsal implant, in accordance with one or more embodiments described herein.
Figure 10B:
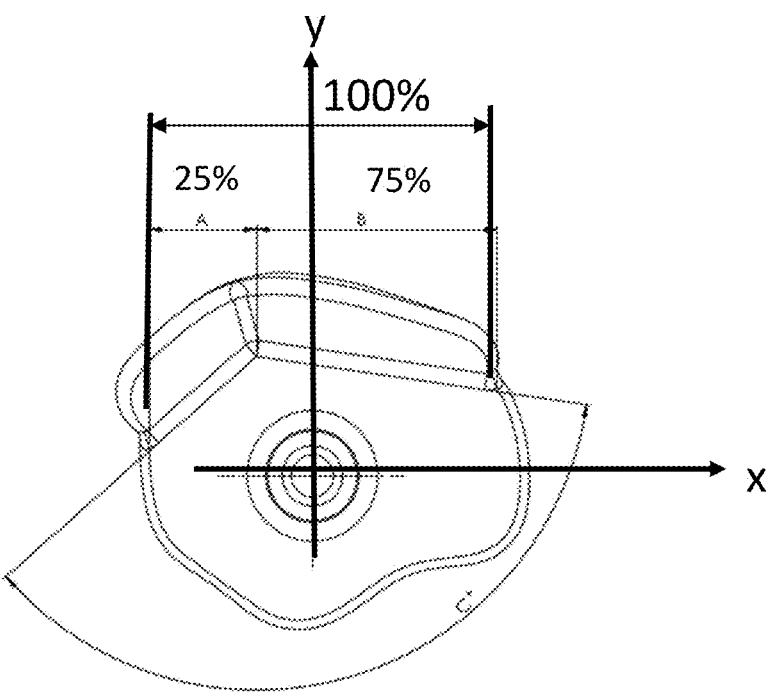

According to embodiments of the present invention, and with reference to FIG. 8a, the projection length A of the lateral flange 1235 is about 0-50% of a total projection length w of the lateral and dorsal flanges 1235 and 1233, or preferably 10-40%, or more preferably 15-35%, or more preferably 20-30%, or more preferably about 25%. In FIG. 10a, the example when the projection length A 0-50% of the total projection length w and accordingly the projection length B of the dorsal flange is 50-100% is of the total projection length w is shown. FIG. 10b illustrates the example when the projection length A is 25% of the total projection length w and accordingly the projection length B of the dorsal flange is 75% is of the total projection length w. Hence, A+B corresponds to the total projected length of the interfaces between the flanges and the metatarsal head surface projected on the x-axis, or in the xy-plane. The projection length A corresponds to an interface 1238 between the lateral flange 1235 and the metatarsal head surface 1231 projected along the x-axis, or in the xy-plane, as illustrated in FIGS. 8a and 8b. Similarly, the projection length B corresponds to an interface 1239 between the dorsal flange 1233 and the metatarsal head surface 1231 projected onto the x-axis, or in the xy-plane, as illustrated in FIGS. 8a and 8b. In other words, the projection length A corresponds to a leg (along the x-axis) and the interface 1238 (in the xy-plane) to the hypotenuse of a right angle triangle. In the same manner, the projection length B corresponds to a leg along the x-axis, or in the xy-plane, and the interface 1239 (in the xy-plane) to the hypotenuse of a right angle triangle.

The metatarsal implant 1200 may be manufactured in a number of different ways, including 3D printing. An articulating surface 1210 of the metatarsal implant 1200 is preferably a metal, metal alloy or ceramic surface, e.g. comprising titanium (Ti), titanium alloy, titanium nitride (TiN), titanium niobium nitride (TiNbN), and/or a cobalt-chromium (CoCr) alloy. It is preferably polished to a perfectly smooth surface, with a very low surface roughness. The bone contacting surface 1230 of the metatarsal implant 1200 may be coated with an osseointegrating and/or bioactive material, such as e.g. hydroxyapatite. The bone contacting surface 1230 of the metatarsal implant 1200 may alternatively be coated with titanium (Ti), titanium alloy, titanium nitride (TiN), or titanium niobium nitride (TiNbN), This reduces the need for using an adhesive for securing the metatarsal implant 1200 to the metatarsal head, but an adhesive (such as e.g. bone cement) may be used anyhow.

The bone contacting surface 1230 and at least a part of a surface area of an implant peg 1220 preferably comprises an osseointegrating structure (shown in FIGS. 3*a*-3*b* as 340), such as e.g. a lattice structure or a random lattice structure. In embodiments of the present invention, the peg is attached to the bone using bone cement in order to fixate the peg in a recess in the bone. Further, the peg 1220 may be screw shaped to allow screwing the peg into the recess of bone and fixating the peg. In other embodiments, the implant peg 1220 may be designed for press-fit into a recess in the metatarsal bone. The peg 1220 of the implant 1200 is preferably designed for press-fit into a recess in the bone. The peg 1220 of the implant 1200 may be tapered at the end, for easier insertion into the recess. If an adhesive such as e.g. bone cement is used, it may not be necessary for the peg 1220 to be designed for press-fit into the recess. The use of press-fit (where the implant peg is slightly larger than the recess) secures the implant 1200 to the implant receiving surface on the metatarsal head regardless of whether an adhesive such as bone cement is used, but the combination of press-fit and adhesive of course secures the implant even more to the implant receiving surface. The implant 1200 may comprise one or more recesses for bone cement in the peg, which secures the implant 1200 even further.

The metatarsal implant 1200 may also comprise a positioning mark (shown in FIG. 2*b*) preferably positioned on the articulating surface 1210. This makes it easier to accomplish a correct rotational positioning of the implant during surgery, which may be important because the articulating surface of the implant will in most situations not be rotationally symmetric. The positioning mark 260 (see FIG. 2*b*) may e.g. be a rotational positioning mark, or an indication of a direction in relation to the anatomy of the joint.

The surface curvature of the articulating surface 1210 of the metatarsal implant 1200 preferably corresponds as closely as possible to a simulated healthy surface curvature of the damaged metatarsal head, and in the embodiment of FIGS. 8*a*-8*b* also extends far enough to always interact with the sesamoid bones, even when the toe is straight. In this way, full account is taken of the sesamoid bones, which move around the metatarsal head as the toe is bent. This increases the possibility of the patient being given back a full range of motion.

By analyzing the surface curvature of the cartilage and/or the bone in a predetermined area comprising and surrounding the site of diseased cartilage, it is possible to simulate a healthy articulating surface of the damaged metatarsal head, generated based on a determined surface curvature of the cartilage and/or the bone in a predetermined area at a site of diseased cartilage and/or bone, to mimic the original, undamaged, articulating surface of the metatarsal head. Image data may be analyzed in a data processing system to identify and determine physical parameters for the cartilage and/or bone damage. The physical parameters to be determined may comprise the presence, the location and the size and shape of the cartilage and/or bone damage, as well as curvature of the surface contour of the cartilage or the bone in an area of the cartilage and/or bone damage. This will be described in more detail below with reference to FIG. 9.

When such a healthy articulating metatarsal surface has been simulated, it is possible to design an individualized metatarsal implant 1200 with an articulating surface 1210 that corresponds to the simulated healthy metatarsal surface.

However, it is also possible to select the best match to the simulated healthy articulating surface of the damaged metatarsal head from a predefined set of predetermined contour curvatures. This enables the use of standardized metatarsal implants 1200. In this way, a set of standardized metatarsal implants 1200 of different dimensions may be manufactured and stored, to be later used for repairing damage in the MTP joint.

A standardized metatarsal implant 1200 may in this case be selected from a predefined set of standardized metatarsal implants 1200 having varying dimensions and geometries. The predefined set of standardized metatarsal implants 1200 is preferably created by analyzing dimensional data from stored images of the metatarsal head from a large number of different patients. The standardized metatarsal implant 1200 should be selected as a standardized metatarsal implant 1200 having dimensions that match the shape of the metatarsal head of the patient, thereby making it suitable for repairing the determined damage. A 3D model of the MTP joint, visualizing the determined damage, may be used in order to determine which standardized metatarsal implant 1200 is the best fit for the metatarsal head of the patient.

However, even if it is possible to use a standardized metatarsal implant 1200, there will always be cases where it cannot be ascertained that a standardized metatarsal implant 1200 will really fit the implant receiving surface on the metatarsal head and repair the damage while taking full account of the sesamoid bones. In order to ascertain that the metatarsal implant 1200 will really fit the implant receiving surface on the metatarsal head, and repair the damage while taking full account of the sesamoid bones, it is necessary to design an individualized metatarsal implant 1200 with an articulating surface 1210 that corresponds to the simulated healthy metatarsal surface, which may also extend far enough to always interact with the sesamoid bones.

Figure 9A:
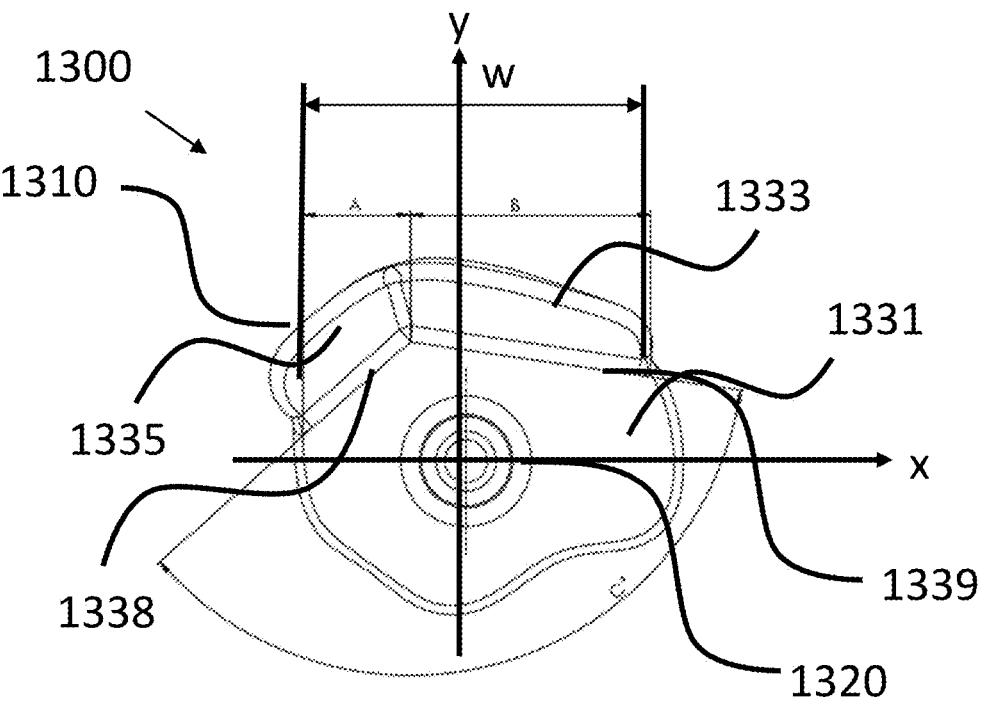
FIGS. 9a-9b illustrate further embodiments of a metatarsal implant, in accordance with one or more embodiments described herein.
Figure 9B:
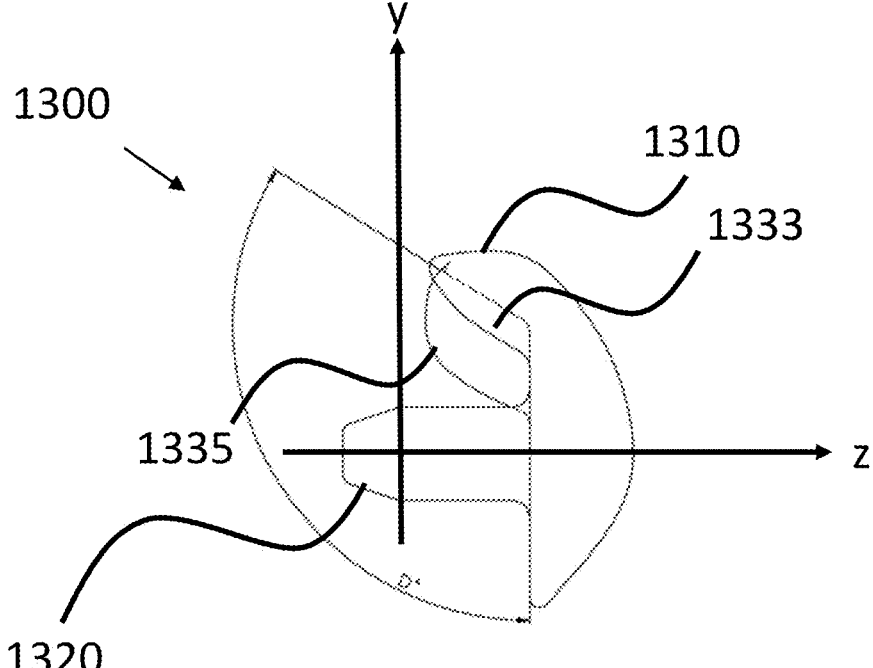

With reference now to FIGS. 9*a*-9*bc*, preferred embodiments of the present invention including a lateral flange will be discussed and shown. The metatarsal implant 1300 comprises a bone contacting surface 1330 shaped to fit an implant receiving surface which has been created on a metatarsal head by mechanical preparation of the metatarsal head to create at least two different planes or surfaces. In the embodiment, shown in FIG. 9*a*, the bone contacting surface 1330 comprises a lateral flange or surface 1335, a dorsal flange or surface 1333 and a metatarsal head surface 1331 in different planes. The lateral surface or flange 1335 is adapted to at least partly coat or cover a lateral side of the metatarsal head and the dorsal flange 1333 is adapted to at least partly coat the dorsal side of the metatarsal head. The predetermined implant angle C in xy-plane between the lateral flange 1335 and a dorsal flange 1333 mainly coating a dorsal side of the metatarsal head is preferably between 90-180°.

According to embodiments of the present invention, and with reference to FIG. 9a, a projection length A of the lateral flange 1335 along the x-axis, or in the xy-plane, is about 0-50% of a total projection length w of the lateral and dorsal flanges 1335 and 1333, or preferably 10-40%, or more preferably 10-40%, or more preferably 20-30%, or more preferably about 25%. In FIG. 10a, the example when the projection length A is 0-50% of the total projection length w and accordingly the projection length B of the dorsal flange is 50-100% is of the total projection length w is shown. FIG. 10b illustrates the example when the projection length A is 25% of the total projection length w and accordingly the projection length B of the dorsal flange is 75% is of the total projection length w. Hence, A+B corresponds to the total projected length of the interfaces between the flanges and the metatarsal head surface projected on the x-axis, or in the xy-plane. The projection length A corresponds to an interface 1338 between the lateral flange 1335 and the metatarsal head surface 1331 projected onto the x-axis or in the xy-plane as illustrated in FIGS. 9a and 9b. Similarly, the projection length B corresponds to an interface 1339 between the dorsal flange 1333 and the metatarsal head surface 1331 projected onto the x-axis, or in the xy-plane, as illustrated in FIGS. 9a and 9b. In other words, the projection length A corresponds to a leg of a first right angle triangle and the interface 1338 to the hypotenuse of the first right angle triangle. In the same manner, the projection length B corresponds to a leg of a second right angle triangle and the interface 1339 to the hypotenuse of the second right angle triangle. Further, with reference to FIG. 9b, the angle D, in the yz-plane, between metatarsal head surface 1331 and the inner surface of the dorsal flange 1333 is preferably >90 degrees.

The metatarsal implant 1300 may be manufactured in a number of different ways, including 3D printing. An articulating surface 1310 of the metatarsal implant 1300 is preferably a metal, metal alloy or ceramic surface, e.g. comprising titanium (Ti), titanium alloy, titanium nitride (TiN), titanium niobium nitride (TiNbN), and/or a cobalt-chromium (CoCr) alloy. It is preferably polished to a perfectly smooth surface, with a very low surface roughness, to lower the risk of a sesamoid bone locking against the articulating surface of the metatarsal implant 1300. The bone contacting surface 1330 of the metatarsal implant 1300 may be coated with an osseointegrating and/or bioactive material, such as e.g. hydroxyapatite. The bone contacting surface 1330 of the metatarsal implant 1300 may alternatively be coated with titanium (Ti), titanium alloy, titanium nitride (TiN), or titanium niobium nitride (TiNbN), This reduces the need for using an adhesive for securing the metatarsal implant 1300 to the metatarsal head, but an adhesive (such as e.g. bone cement) may be used anyhow.

The bone contacting surface 1330 and at least a part of a surface area of an implant peg 1320 preferably comprises an osseointegrating structure (shown in FIGS. 3a-3b as 340), such as e.g. a lattice structure or a random lattice structure. In embodiments of the present invention, the peg is attached to the bone using bone cement in order to fixate the peg in a recess in the bone. Further, the peg 1320 may be screw shaped to allow screwing the peg into the recess of bone and fixating the peg. In other embodiments, the implant peg 1300 may be designed for press-fit into a recess in the metatarsal bone. The peg 1320 of the implant 1300 is preferably designed for press-fit into a recess in the bone. The peg 1320 of the implant 1300 may be tapered at the end, for easier insertion into the recess. If an adhesive such as e.g. bone cement is used, it may not be necessary for the peg

1320 to be designed for press-fit into the recess. The use of press-fit (where the implant peg is slightly larger than the recess) secures the implant 1300 to the implant receiving surface on the metatarsal head regardless of whether an adhesive such as bone cement is used, but the combination of press-fit and adhesive of course secures the implant even more to the implant receiving surface. The implant 1300 may comprise one or more recesses for bone cement in the peg, which secures the implant 1300 even further.

The metatarsal implant 1300 may also comprise a positioning mark (shown in FIG. 2b) preferably positioned on the articulating surface 1310. This makes it easier to accomplish a correct rotational positioning of the implant during surgery, which may be important because the articulating surface of the implant will in most situations not be rotationally symmetric. The positioning mark 260 (see FIG. 2b) may e.g. be a rotational positioning mark, or an indication of a direction in relation to the anatomy of the joint.

The surface curvature of the articulating surface 1310 of the metatarsal implant 1300 preferably corresponds as closely as possible to a simulated healthy surface curvature of the damaged metatarsal head, and in the embodiment of FIGS. 9a-9b also extends far enough to always interact with the sesamoid bones, even when the toe is straight. In this way, full account is taken of the sesamoid bones, which move around the metatarsal head as the toe is bent. This increases the possibility of the patient being given back a full range of motion.

By analyzing the surface curvature of the cartilage and/or the bone in a predetermined area comprising and surrounding the site of diseased cartilage, it is possible to simulate a healthy articulating surface of the damaged metatarsal head, generated based on a determined surface curvature of the cartilage and/or the bone in a predetermined area at a site of diseased cartilage and/or bone, to mimic the original, undamaged, articulating surface of the metatarsal head. Image data may be analyzed in a data processing system to identify and determine physical parameters for the cartilage and/or bone damage. The physical parameters to be determined may comprise the presence, the location and the size and shape of the cartilage and/or bone damage, as well as curvature of the surface contour of the cartilage or the bone in an area of the cartilage and/or bone damage. This will be described in more detail below with reference to FIG. 9.

When such a healthy articulating metatarsal surface has been simulated, it is possible to design an individualized metatarsal implant 1300 with an articulating surface 1310 that corresponds to the simulated healthy metatarsal surface.

However, it is also possible to select the best match to the simulated healthy articulating surface of the damaged metatarsal head from a predefined set of predetermined contour curvatures. This enables the use of standardized metatarsal implants 1300. In this way, a set of standardized metatarsal implants 1200 of different dimensions may be manufactured and stored, to be later used for repairing damage in the MTP joint.

A standardized metatarsal implant 1300 may in this case be selected from a predefined set of standardized metatarsal implants 1300 having varying dimensions and geometries. The predefined set of standardized metatarsal implants 1300 is preferably created by analyzing dimensional data from stored images of the metatarsal head from a large number of different patients. The standardized metatarsal implant 1300 should be selected as a standardized metatarsal implant 1300 having dimensions that match the shape of the metatarsal head of the patient, thereby making it suitable for repairing the determined damage. A 3D model of the MTP joint, visualizing the determined damage, may be used in order to determine which standardized metatarsal implant 1300 is the best fit for the metatarsal head of the patient.

However, even if it is possible to use a standardized metatarsal implant 1300, there will always be cases where it cannot be ascertained that a standardized metatarsal implant 1300 will really fit the implant receiving surface on the metatarsal head and repair the damage while taking full account of the sesamoid bones. In order to ascertain that the metatarsal implant 1300 will really fit the implant receiving surface on the metatarsal head, and repair the damage while taking full account of the sesamoid bones, it is necessary to design an individualized metatarsal implant 1300 with an articulating surface 1310 that corresponds to the simulated healthy metatarsal surface, which may also extend far enough to always interact with the sesamoid bones.

Where applicable, various embodiments provided by the present disclosure can be implemented using hardware, software, or combinations of hardware and software. Also where applicable, the various hardware components and/or software components set forth herein can be combined into composite components comprising software, hardware, and/ or both without departing from the claimed scope of the present disclosure. Where applicable, the various hardware components and/or software components set forth herein can be separated into sub-components comprising software, hardware, or both without departing from the claimed scope of the present disclosure. In addition, where applicable, it is contemplated that software components can be implemented as hardware components, and vice-versa. The method steps of one or more embodiments described herein may be performed automatically, by any suitable processing unit, or one or more steps may be performed manually. Where applicable, the ordering of various steps described herein can be changed, combined into composite steps, and/or separated into sub-steps to provide features described herein.

Software in accordance with the present disclosure, such as program code and/or data, can be stored in non-transitory form on one or more machine-readable mediums. It is also contemplated that software identified herein can be implemented using one or more general purpose or specific purpose computers and/or computer systems, networked and/or otherwise.

In embodiments, there is provided a computer program product comprising computer readable code configured to, when executed in a processor, perform any or all of the method steps described herein. In some embodiments, there are provided a non-transitory computer readable memory on which is stored computer readable and computer executable code configured to, when executed in a processor, perform any or all of the method steps described herein.

In one or more embodiments, there is provided a non-transitory machine-readable medium on which is stored machine-readable code which, when executed by a processor, controls the processor to perform the method of any or all of the method embodiments presented herein.

The foregoing disclosure is not intended to limit the present invention to the precise forms or particular fields of use disclosed. It is contemplated that various alternate embodiments and/or modifications to the present invention, whether explicitly described or implied herein, are possible in light of the disclosure. Accordingly, the scope of the invention is defined only by the claims.

The invention claimed is:

1. A metatarsal implant for repairing damage in a metatarsophalangeal joint of a patient, the metatarsal implant being adapted to be attached to at least two implant receiving surfaces which have been created on a metatarsal head of the patient by mechanical preparation, the metatarsal implant comprising:

bone contacting surfaces designed to correspond to the implant receiving surfaces, wherein the bone contacting surfaces comprise:

at least two different sub-surfaces, including a lateral surface adapted to at least partly coat a lateral side of the metatarsal head and a dorsal surface adapted to at least partly coat a dorsal side of the metatarsal head, in different planes with a predetermined implant angle therebetween, wherein said metatarsal implant is designed not to include any additional subsurface extending onto a medial side of the metatarsal head so as to not cover any of the medial side of the metatarsal head.

2. The metatarsal implant according to claim 1, wherein a projection length of a lateral flange is about 0-50% of a total projection length of the lateral flange and dorsal flange, where the total projected length is the length of interfaces between the lateral and dorsal flanges, respectively, and the metatarsal head surface projected on along an x-axis, or in the xy-plane, in a three-dimensional coordinate system.

3. The metatarsal implant according to claim 1, wherein a contour curvature of an articulating surface of the metatarsal implant is designed to repair the metatarsal head, generated based on a determined surface curvature of cartilage and/or bone in a predetermined area at a site of diseased cartilage and/or bone, to mimic an original, undamaged, articulating surface of the metatarsal head.

4. The metatarsal implant according to claim 1, wherein the predetermined implant angle between the lateral surface and the dorsal surface coating a dorsal side of the metatarsal head is between 90-180°.

5. The metatarsal implant according to claim 1, wherein the metatarsal implant is adapted to be attached to the implant receiving surfaces which have been created on the metatarsal head by removing sections of the metatarsal head in at least two different planes, where the bone contacting surface of the metatarsal implant is designed to correspond to the implant receiving surfaces.

6. The metatarsal implant according to claim 1, wherein the bone contacting surface comprising at least three different sub-surfaces in different planes, and at least one junction point where three sub-surfaces meet, and a contour curvature of an articulating surface of the metatarsal implant is designed by simulating a healthy articulating surface of the metatarsal head, generated based on a determined surface curvature of cartilage and/or bone in a predetermined area at a site of diseased cartilage and/or bone, to mimic an original, undamaged, articulating surface of the metatarsal head.

7. The metatarsal implant according to claim 1, where a contour curvature of an articulating surface of the metatarsal implant is designed to correspond to a simulated healthy articulating surface of the metatarsal head at a site of diseased cartilage and/or bone.

8. The metatarsal implant according to claim 1, where a contour curvature of an articulating surface of the metatarsal implant is selected from a predefined set of predetermined contour curvatures, as a best match to a simulated healthy articulating surface of the metatarsal head.

9. The metatarsal implant according to claim 1, further comprising an implant peg extending from the bone contacting surfaces of the metatarsal implant, wherein the bone contacting surfaces and at least a part of a surface area of the implant peg comprises an osseointegrating structure.

10. The metatarsal implant according to claim 1, wherein an articulating surface of the metatarsal implant comprises a positioning mark.

11. The metatarsal implant according to claim 1, wherein the implant receiving surfaces on the metatarsal head can be created by drilling, milling, and/or sawing the implant receiving surfaces using a metatarsal preparation guide tool.

12. A metatarsophalangeal implant arrangement for repairing damage in a metatarsophalangeal joint of a patient, the metatarsophalangeal implant arrangement comprising a phalangeal implant, comprising an articulating surface, and a metatarsal implant adapted to be attached to at least two implant receiving surfaces which have been created on a metatarsal head of the patient by mechanical preparation, wherein the implant receiving surfaces have a predetermined implant angle therebetween, wherein bone contacting surfaces of the metatarsal implant are designed to correspond to the implant receiving surfaces, wherein the bone contacting surfaces comprise:

at least two different sub-surfaces in different planes with a predetermined angle therebetween, wherein one of the at least two different sub-surfaces is a lateral sub-surface, and wherein the articulating surface of the phalangeal implant and an articulating surface of the metatarsal implant are designed to allow that they interact with each other when the implants are implanted into the metatarsophalangeal joint of the patient, wherein said metatarsal implant is designed not to include any additional subsurface extending onto a medial side of the metatarsal head so as to not cover any of the medial side of the metatarsal head.

13. The metatarsophalangeal implant arrangement according to claim 12, wherein the articulating surface of the metatarsal implant is a metal, metal alloy, or ceramic surface.

14. The metatarsophalangeal implant arrangement according to claim 12, wherein the articulating surface of the phalangeal implant is not a metal, metal alloy or ceramic surface.

15. The metatarsophalangeal implant arrangement according to claim 12, wherein the lateral sub-surface is adapted to at least partly coat a lateral side of the metatarsal head.

16. The metatarsophalangeal implant arrangement according to claim 12, wherein the predetermined angle between the lateral sub-surface and a dorsal sub-surface adapted to at least partly coat a dorsal side of the metatarsal head is between 90-180°.

17. The metatarsophalangeal implant arrangement according to claim 12, wherein the articulating surface of the metatarsal implant comprises titanium (Ti) or titanium alloy, titanium nitride (TiN) titanium niobium nitride (TiNbN), and/or a cobalt-chromium (CoCr) alloy.

18. The metatarsophalangeal implant arrangement according to claim 12, wherein the articulating surface of the phalangeal implant comprises a polymer material.

19. The metatarsophalangeal implant arrangement according to claim 12, wherein the phalangeal implant comprises a bone contacting surface comprising titanium (Ti) or titanium alloy, titanium nitride (TiN), titanium niobium nitride (TiNbN), and/or a cobalt-chromium (CoCr) alloy.

20. The metatarsophalangeal implant arrangement according to claim 12, wherein the implant receiving surfaces on the metatarsal head can be created by drilling, milling, and/or sawing the implant receiving surfaces using a metatarsal preparation guide tool.

21. A metatarsal implant for repairing damage in a metatarsophalangeal joint of a patient, the metatarsal implant being adapted to be attached to at least three implant receiving surfaces which have been created on a metatarsal head of the patient by mechanical preparation, the metatarsal implant comprising:

bone contacting surfaces designed to correspond to the implant receiving surfaces, wherein the bone contacting surfaces comprise:

at least three different sub-surfaces, including a metatarsal head sub-surface adapted to at least partly coat a metatarsal head surface, a lateral sub-surface adapted to at least partly coat a lateral side of the metatarsal head and a dorsal surface adapted to at least partly coat a dorsal side of the metatarsal head, each sub-surface being in different planes wherein a majority of the circumference surrounding the metatarsal head sub-surface has no interface with a sub-surface extending in a different plane from that of the metatarsal head sub-surface.

* * * * *